(12) United States Patent
Cheng

(10) Patent No.: US 9,249,098 B2
(45) Date of Patent: Feb. 2, 2016

(54) DERIVATIVES OF DONEPEZIL

(76) Inventor: Xueheng Cheng, Libertyville, IL (US)

( * ) Notice: Subject to any disclaimer, the term of this patent is extended or adjusted under 35 U.S.C. 154(b) by 0 days.

(21) Appl. No.: 14/410,835

(22) PCT Filed: Jul. 10, 2012

(86) PCT No.: PCT/CN2012/078415
§ 371 (c)(1),
(2), (4) Date: Dec. 23, 2014

(87) PCT Pub. No.: WO2014/008629
PCT Pub. Date: Jan. 16, 2014

(65) Prior Publication Data
US 2015/0225343 A1    Aug. 13, 2015

(51) Int. Cl.
*A61K 31/445* (2006.01)
*C07D 211/06* (2006.01)
*C07D 211/32* (2006.01)
*A61K 45/06* (2006.01)

(52) U.S. Cl.
CPC ............ *C07D 211/32* (2013.01); *A61K 31/445* (2013.01); *A61K 45/06* (2013.01)

(58) Field of Classification Search
None
See application file for complete search history.

(56) References Cited

U.S. PATENT DOCUMENTS 6,677,330 B1 *    1/2004   Iimura et al. .................. 514/183
2009/0137629 A1 *  5/2009   Iimura et al. .................. 514/319

OTHER PUBLICATIONS

CAPLUS 2001:413185.*
CAPLUS 1997:678673.*

* cited by examiner

*Primary Examiner* — Heidi Reese
(74) *Attorney, Agent, or Firm* — Justin Lampel

(57) ABSTRACT

This invention relates to novel compounds and hydrochloric acid salts thereof. More specifically, this invention relates to novel compounds and hydrochloric acid salts thereof derived from donepezil. This invention also provides compositions comprising one or more compounds of this invention and a carrier and the use of the disclosed compounds and compositions in methods of treating diseases and conditions that are beneficially treated by administering an acetylcholinesterase (AChE) inhibitor, such as donepezil.

6 Claims, 2 Drawing Sheets

Figure 1. Rat pharmacokinetics measurement for donepezil (1-A) and compound IV-8 (1-B) with intravenous (IV) and oral (PO) dosing.
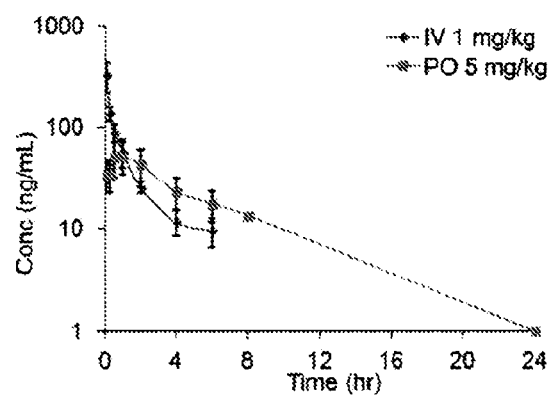
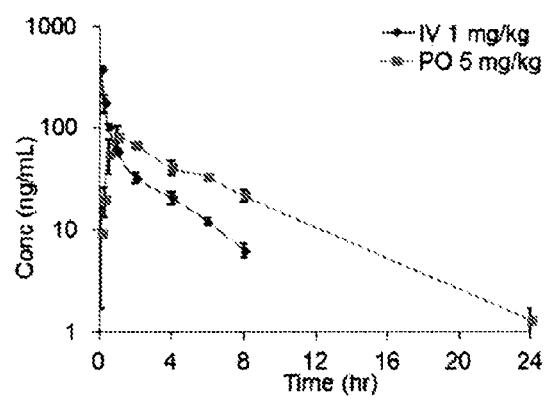
Fig. 1-A        Fig. 1-B Figure 2. Water maze memory restoration effect. EX-1601 = compound IV-8.
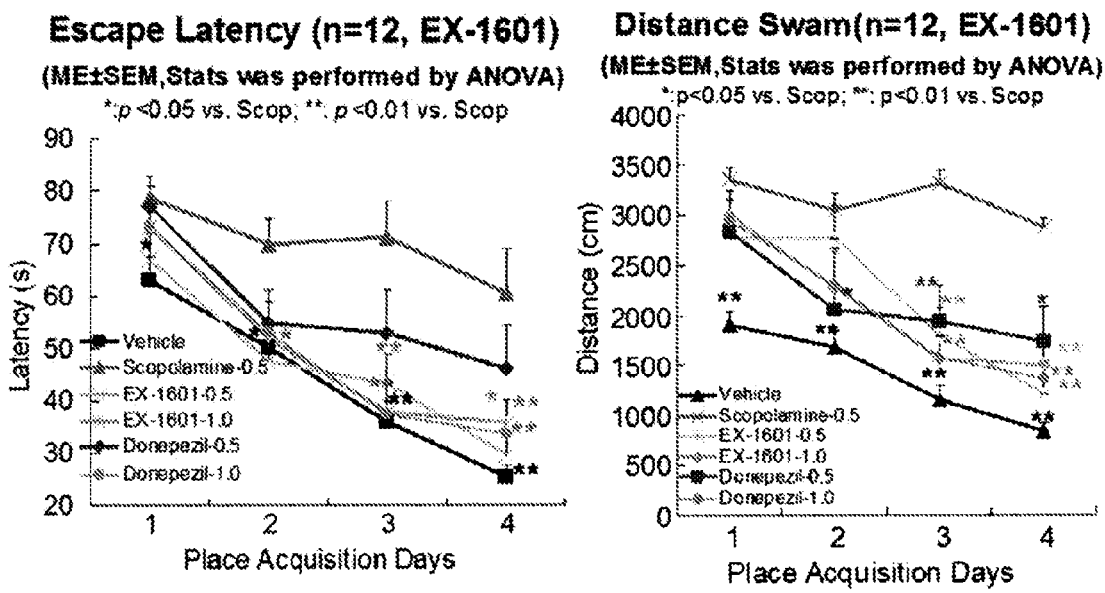
Fig. 2-A
Fig. 2-B
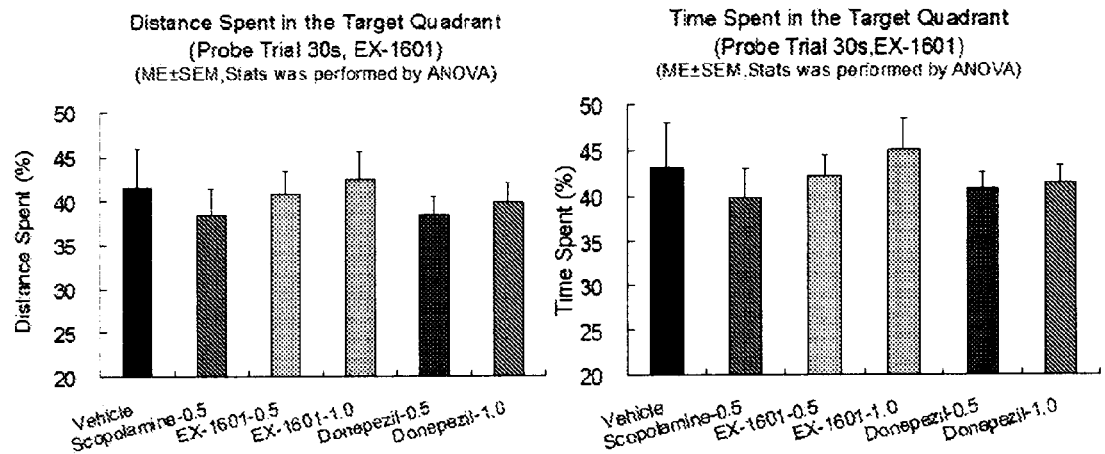
Fig. 2-C
Fig. 2-D

9,249,098 B2

DERIVATIVES OF DONEPEZIL

FIELD OF THE INVENTION

Compounds derived from donepezil, pharmaceutical compositions containing derivatives of donepezil, and methods of using the same are provided.

CROSS REFERENCE TO RELATED APPLICATIONS

The following application is based on and claims the priority benefit of PCT Application No.: PCT/CN2012/078415 filed on Jul. 10, 2012 currently co-pending; the entire contents of which are incorporated by reference.

BACKGROUND OF THE INVENTION

Donepezil, also known as Aricept™, or 2-((1-benzylpiperidin-4-yl)methyl)-5,6-dimethoxy-2,3-dihydro-1H-inden-1-one, is a centrally acting reversible acetylcholinesterase (AChE) inhibitor. Its main therapeutic use is in the treatment of Alzheimer's disease where it is used to increase levels of cortical acetylcholine. See US FDA label for Aricept @http://www.accessdata.fda.gov/drugsaifda_docs/label/2006/020690s026,021720s003lbl.pdf Donepezil is currently approved for treatment of Alzheimer's disease. Despite the beneficial activities of donepezil, there is a continuing need for new compounds to treat Alzheimer's diseases and conditions. It is desirable to discover novel derivatives thereof. Donepezil is described in U.S. Pat. Nos. 4,895,841 and 7,727,548, the contents of which are incorporated herein by reference.

SUMMARY OF THE INVENTION

Compounds and hydrochloric acid salts thereof derived from donepezil are provided. The compounds derived herein, or a mixture of compounds derived herein, and a carrier may be used in treating diseases and other conditions. More specifically, the diseases and other conditions may be treated by administering an acetylcholinesterase (ACNE) inhibitor, such as donepezil.

BRIEF DESCRIPTION OF THE DRAWINGS

FIGS. 1A and 1B shows plot of plasma concentration vs. time for donepezil and compound IV-8 with intravenous (IV) and oral (PO) dosing on SD rats.

FIGS. 2A, 2B, 2C and 2D shows experimental data for compound IV-8.

DETAILED DESCRIPTION OF THE INVENTION

Derivatives of donepezil and compositions comprising derivatives of donepezil are provided herein.

In one embodiment, the derivatives of donepezil provide novel compounds of formula I-III or a pharmaceutically acceptable salt thereof,

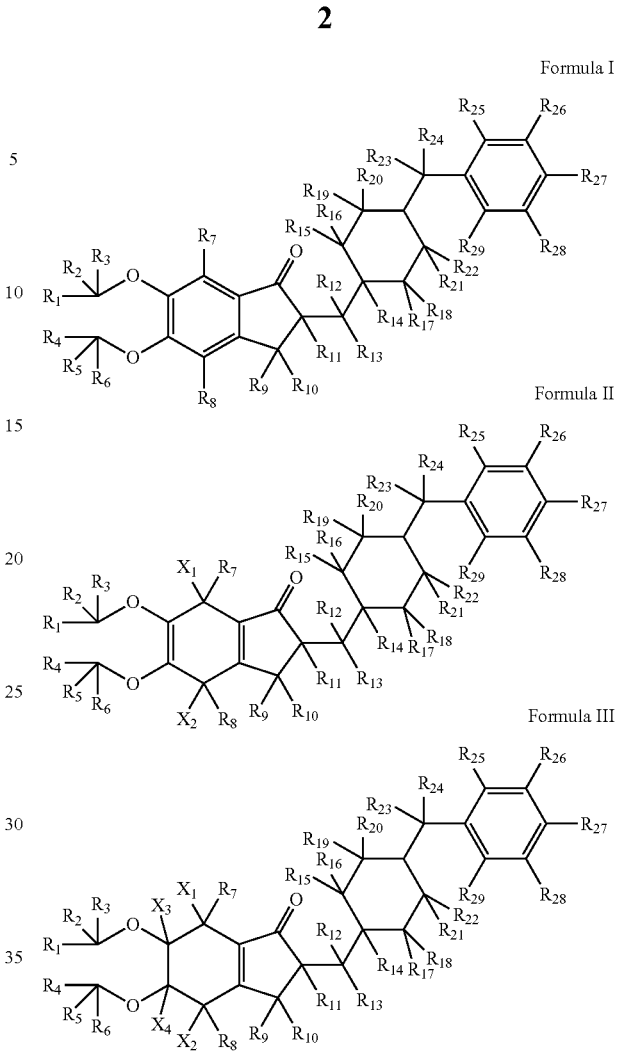

wherein R1-R29 and X1-X4 are independently selected from hydrogen, deuterium, methyl, lower alkyl, methoxy, lower alkoxy, aryloxy, trifluoromethyl, trifluoromethoxy, cyano, nitro, amino, lower alkylamino, lower dialkylamino, mercapto, lower alkylthio, arylthio, formyl, acetyl, lower alkylcarbonyl, arylcarbonyl, formate, lower alkylcarboxy, arylcarboxy, lower alkoxylcarboxy, aryloxylcarboxy, formamido, lower alkanoylamino, arylcarbonylamino, carbamido, lower alkylcarbamido, arylcarbamido, animocaboxy, lower alkylaminocarboxy, arylaminocarboxy, trifluoroacetyl, halogen, hydroxylcarbonyl, lower alkoxylcarbonyl, aryloxycarbonyl, solfinyl, lower alkylsolfinyl, arylsulfinyl, sulfonyl, lower alkylsulfonyl, arylsulfonyl, sulfonamido, lower alkylsulfonamido, arylsulfonamido, and aryl functional groups. At least one functional group among R1-R29 in formula I-III is not hydrogen.

In another embodiment, the derivatives of donepezil provide novel compounds of formula I-III or a pharmaceutically acceptable salt thereof, wherein R1-R29 and X1-X4 are independently selected from hydrogen, fluorine, chlorine, or hydroxyl functional groups. At least one functional group among R1-R29 in formula I-III is not hydrogen.

In another embodiment, the derivatives of donepezil provide novel pharmaceutical compositions, comprising a pharmaceutically acceptable carrier and a therapeutically effective amount of a compound of formula I-III.

In another embodiment, the derivatives of donepezil provide a method for treating Alzheimer's disease comprising: administering to a patient in need thereof a therapeutically effective amount of compound of formula I-III.

In another embodiment, the derivatives of donepezil may be used in therapy (e.g., for the treatment of Alzheimer's disease).

In another embodiment, the derivatives of donepezil may be used for the manufacture of a medicament (e.g., for the treatment of Alzheimer's disease).

The present invention may be embodied in other specific forms without departing from the spirit or essential attributes thereof. It is understood that any and all embodiments of the invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

The compounds of formula I-III may have asymmetric centers. Compounds of formula I-III containing an asymmetrically substituted atom may be isolated in optically active or racemic forms. It is well known in the art how to prepare optically active forms, such as by resolution of racemic forms or by synthesis from optically active starting materials. All optical isomers of shown or described compounds are considered to be part of the present invention. All tautomers, salts, hydrates, solvated forms of shown or described compounds are also considered to be part of the present invention.

The compounds of formula I-III may form metabolites after administered into human such as N-oxides and other oxidation products by endogeneous cytochrom P450 enzymes. Some of the metabolites may possess inhibitory activity against AChE and therefore may have anti-Alzheimer's disease effect. All metabolites of shown or described compounds are also considered to be part of the present invention. All prodrugs of shown or described compounds are also considered to be part of the present invention.

Definitions. The examples provided in the definitions present in this application are non-inclusive unless otherwise stated. They include but are not limited to the recited examples.

Throughout this specification, a variable may be referred to generally (e.g., "each R" or "each X") or may be referred to specifically (e.g., R1, R2, R3, X1, X2, etc.). Unless otherwise indicated, when a variable is referred to generally, it is meant to include all specific embodiments of that particular variable.

The term "halogen" refers to any of —Cl, —F, —Br, or —I.
The term "carboxy" refers to —C(O)O—
The term "oxo" refers to =O.
The term "alkoxy" refers to —O-alkyl.
The term "alkylamino" refers to —NH-alkyl.
The term "dialkylamino" refers to —N(alkyl)-alkyl, wherein the two alkyl moieties are the same or different.

The term "alkyl" refers to straight or branched chains of carbon atoms, "lower alkyl" refers to straight or branched alkyl chains of from 1 to 12 carbon atoms, unless otherwise specified. Examples of straight chained and branched lower alkyl groups include methyl, ethyl, n-propyl, iso-propyl, n-butyl, sec-butyl, tort-butyl, pentyl, hexyl, pentyl and octyl. The alkyl group can contain substitution groups on the carbon chain.

The term "aryl" refers to optionally substituted carbocyclic aromatic groups such as phenyl and naphthyl. Suitable substituents on an aryl can include, but are not limited to for example, alkyl, halogen, cyano, hydroxyl, carboxy, alkoxy, amino, alkylamino and dialkylamino. The aryl group can contain one or more heteroatoms such as nitrogen, oxygen or sulfur in the ring.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. "Therapeutically effective amount" includes an amount of a compound of the present invention that is effective when administered alone or in combination to treat the desired condition or disorder.

"Pharmaceutically acceptable salts" refer to any non-toxic salt that, upon administration to a recipient, is capable of providing, either directly or indirectly, a compound of this invention. Examples of pharmaceutically acceptable salts include, but are not limited to, mineral or organic acid salts of the basic residues. The pharmaceutically acceptable salts include the conventional quaternary ammonium salts of the parent compound formed, for example, from non-toxic inorganic or organic acids. For example, such conventional non-toxic salts include, but are not limited to, those derived from inorganic and organic acids selected from 1, 2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluenesulfonic, naphthalenesulfonic, mandelic, and other acids.

"Prodrug" refers to a pharmacologically inactive compound, for example, the temporary derivatization of a functional group of an active drug, which is converted into the active drug after administration. For example, it may be an inactive compound that can produce the active drug when metabolized in the body. See references: A. L. Simplicio, et al., Prodrugs for Amines, Molecules 2008, 13, 519-547.

The compounds of the present invention may be discovered by non-selective chemical modifications of donepezil to form a derivative product mixture and identification of components of the derivative product mixture possessing improved properties. The novel compounds may be useful as therapies for the treatment of Alzheimer's disease and other neurodegenerative diseases and neuro-disorders.

Suitable methods were previously developed to generate non-selective chemical modification product mixtures from a compound of pharmaceutical utility and to screen the derivative product mixture to identify compounds possessing improved properties. Selected compounds can be purified from the derivative product mixture and their chemical identity can be determined by using chemical structure analysis techniques such as nuclear magnetic resonance (NMR) and mass spectrometry (MS). The previous techniques of non-selective chemical modification, preparation of derivative compound mixture (mixture compound libraries) and screening of the mixture compounds libraries for the discovery of compounds possessing improved properties were described in U.S. Patent Application Ser. Nos. 61/281,371 and 12/946,533, the contents of which are incorporated herein by reference.

The mixture compound libraries may be prepared from the reaction of donepezil with elemental fluorine (in the form of mixture with high purity nitrogen) at a low temperature in an organic solvent. The mixture compound libraries may also be prepared with elemental fluorine and in the presence of a reagent that can donate a functional group during reaction with elemental fluorine. Generally, the reaction is performed in an inert organic solvent such as dichloromethane and acetonitrile.

Compounds of this invention may be obtained by chromatographic separation and purification using HPLC equipment from the mixture compound libraries. Separation can be done more than once to increase the purity of the compound so obtained. Structural identities of the compounds may be determined, after purification, by NMR and mass spectrometry techniques. Structural identity of the compounds of this invention may also be determined in the mixture compound libraries, without purification, by LC-MS/MS and LC-NMR techniques.

Upon determination of the structural identity, the compounds of this invention may also be prepared by organic synthesis methodologies that are within the knowledge of those skilled in the art of organic synthesis.

Formation of the salt form can be done by adding a corresponding acid to the free base compound solution in a suitable organic solvent, progressively reducing the amount of solvent. By working in this manner, the salt of the compound of this invention can be extracted from the mother liquors of crystallization by those skilled in the art of crystallization.

The present invention relates to pharmaceutical compositions containing one or more of pharmaceutically acceptable salts, in the pure state or in the presence of a diluent or a coating. These compositions may be employed orally or through other administration methods as solid compositions for oral administration. In addition, tablets, pills, powders or granules may be used. In these compositions, the active product according to the invention is mixed with one or more inert diluents such as sucrose, lactose or starch. These compositions can also comprise substances other than diluents, e.g. a lubricant or a component modulating the release, absorption or stability of the active product.

As liquid compositions for oral administration, solutions, suspensions, syrups, elixirs and pharmaceutically acceptable emulsions, containing inert diluents such as water or liquid paraffin, may be used. These compositions can also comprise substances other than diluents, e.g. wetting, sweetening or flavoring products.

Compositions can be a pharmaceutically acceptable salt of said compound; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The invention also provides a method of treating a disease that is beneficially treated by donepezil in a patient in need thereof comprising the step of administering to said patient an effective amount of a compound or a composition of this invention.

In yet another aspect, the invention provides the use of a compound in a formulation alone or together with one or more additional therapeutic agents, either as a single composition or as separate dosage forms, for treatment or prevention in a patient of a disease, disorder or symptom set forth above.

For the discovery of donepezil derivative compounds possessing improved properties, the following steps may be used.

Preparation of non-selective modification product mixtures of donepezil (mixture compound libraries). 300 mg donepezil was dissolved in 200 mL $CH_2Cl_2$ at −78° C. cooled by dry-ice/acetone bath. A mixture of $F_2$ and $N_2$ gas containing 20% $F_2$/80% $N_2$ was passed through the reaction vessel continuously at a flow rate of 2 L/min. The reaction is stopped after 30 min and the solvent was removed under vacuum. Dried reaction products were dissolved in 20 mL acetonitrile and the solution was analyzed by LC-MS (Agilent 1200, Agilent Eclips 150×4.6 mm column, gradient elution from 10% acetonitrile/90% 0.1% formic acid in dd-$H_2O$ to 90% acetonitril/10% 0.1% formic acid in dd-$H_2O$, 1 ml/min total flow rate, Waters LCT TOFMS in positive ion mode). Non-selective modification products may be distinguished based on HPLC retention time (RT) and molecular weight of the components.

Preparation of mixture derivative compounds for screening. Non-selective modification reaction product mixture of donepezil was separated on an Agilent Zorbax C8 250×4.6 mm column, gradient elution from 30% MeOH/70% 0.1% formic acid in dd-$H_2O$ to 90% MeOH/10% 0.1% formic acid in dd-$H_2O$, 1 ml/min total flow rate. Each fraction was analyzed by LCT mass spectrometer. Some fractions may contain mostly the unreacted donepezil, other fractions may contain various kinds of reaction products along with small amount of unreacted donepezil. Those latter fractions may be mixed to form the modified donepezil compound mixture (mixture compound library) for the subsequent screening.

Screening of mixture compound library to identify compounds with improved properties. The identification of the compounds in the mixture compound library possessing improved properties can be done using procedures similar to that described in a previous invention (U.S. Patent Application Nos. 61/281,371 and 12/946,533, the contents of which are incorporated herein by reference). Specifically the mixture compound library may be screened, in a mixture format, for affinity toward the protein acetylcholinesterase (AChE) using ultrafiltration, for metabolic stability using human liver microsome extraction, and for other pharmaceutical properties including, but not limited to: membrane permeability, plasma protein binding properly, blood-brain-barrier (BBB) penetration property. Derivatives of donepezil possessing improved properties over donepezil itself may be detected from the above screening tests. The identity of the mixture compound library components may be specified as the retention time (RT) and m/z value in LC-MS analysis. Thus any components that are uniquely identified in LC-MS analysis as separate from other components based on retention time (RT) and m/z values can be monitored separately. For such "LC-MS separable" components, it can be determined whether one particular component has a better property than the parent drug donepezil by using LC-MS technique. Similarly NMR or other techniques can be used to determine pharmaceutical properties of the mixture components in the screening tests relative to the parent drug donepezil itself. These mixture format screening tests and measurement methods may allow detection and identification of components possessing improved properties relative to the parent drug donepezil itself.

Affinity screening. Mixture compound library was mixed with a buffered solution containing 10 uM AChE enzyme at pH 7.4 (50 mM Tris HCl). The mixture was filtered through a ultrafiltration microcon filter (Millipore) with molecular weight cutoff (MWCO) of 10 kDa by centrifugation at 12000 rpm for 20 min. New buffer was added to the top of the filter and the solution was filtered through the microcon filter again. This process was repeated several times and a portion of the top layer of each filtration was removed and treated with organic solvent acetonitrile or methanol to denature the enzyme and to extract the donepezil screening library compounds that bound to the enzyme. Compound concentration in the top layer was measured by LC-MS analysis (Agilent 1200, Agilent Eclips 150×4.6 mm, gradient elution from 10% acetonitrile/90% 0.1% formic acid in dd-H2O to 90% acetonitrile/10% 0.1% formic acid in dd-H2O, 1 ml/min total flow rate, Waters LCT TOFMS in positive ion mode), and the relative affinity determined based on the concentration change after each round of filtering through microcon filter. A sample containing the donepezil screening library but without the AChE enzyme was treated the same way as the sample with AChE enzyme to serve as a protein-negative control. The components with larger decrease in concentration in the sample with the AChE enzyme after each filtering indicate lower affinity and vice versa. The affinity screening results allow identification of components of the non-selective modification product mixture that possess improved affinity toward AChE protein relative to donepezil itself. Table 1 lists the affinity of selected compounds of the invention as compared to donepezil in binding to AChE protein.

where the mixture compound library was replaced by pure donepezil and by positive reference compound terfenedine each at 1 uM. The concentration of compounds before and after the microsome incubation was measured by LC-MS analyses (Agilent 1200, Agilent Eclips 150×4.6 min, gradient elution from 10% acetonitrile/90% 0.1% formic acid in dd-H2O to 90% acetonitrile/10% 0.1% formic acid in dd-H2O, 1 ml/min total flow rate, Waters LCT TOFMS in positive ion mode), and the relative metabolic stability determined based on the concentration change after incubation. The components with larger decrease in concentration after microsome incubation indicate lower metabolic stability and vice versa. The metabolic stability testing results allow identification of components of the non-selective modification product mixture that possess improved metabolic stability relative to donepezil itself. Table 2 lists the metabolic stability of selected compounds of the invention as compared to donepezil through incubation with human liver microsome.

TABLE 1

Affinity of selected compounds of this invention toward AChE. The list consists compound formula (m/z, RT in min), relative affinity.

| | | |
|---|---|---|
| M + F(398, 4.04), 1.34; | M + F(398, 4.18), 1.84; | M + 2F(416, 4.14), 1.96; |
| M + 2F(416, 4.27), 2.32; | M + 3F(434, 4.33), 2.76; | M + 3F(434, 4.47), 2.75; |
| M + O(396, 3.96), 0.2; | M + O(396, 4.29), 2.33; | M + O(396, 4.36), 1.88; |
| M + O + F(414, 3.92), 0.88; | M + O + F(414, 4.14), 1.49; | M + O + F(414, 4.2), 0.17; |
| M + O + F(414, 4.46), 2.13; | M + O + 2F(432, 3.98), 0.67; | M + O + 2F(432, 4.25), 1.27; |
| M + O + 2F(432, 4.47), 4.55; | M + F2(418, 3.84), 0.55; | M + 2F2(456, 4.02), 0.39; |
| M + 2F2 + F(474, 4.07), 0.29; | M + 4F(452, 4.51), 3.94; | M + 4F(452, 4.64), 2.02; |
| M + 4F(452, 4.97), 2.96; | M + 4F(452, 5.14), 2.88. | |

M = donepezil.

The relative affinity of donepezil is defined as 1.00.

Liver microsome stability testing. Mixture compound library was mixed with a buffered solution containing human liver microsome (Invitrogen Cat. No. HMMC-PL, 1 mg/ml, diluted from 20 mg/mL stock with buffer), 1 mM NADPH in 50 mM KPO4, 3 mM MgCl2, pH7.4 for 2 hours at 37° C. and then was treated with 3 volumes of organic solvent acetonitrile to stop the metabolism reaction and to extract the screening library compounds. Control samples were also done

TABLE 2

Metabolic stability of selected compounds of this invention. The list consists compound formula (m/z, RT in min), relative metabolic stability.

| | | |
|---|---|---|
| M + F(398, 3.64), 1.35; | M + F(398, 3.74), 1.52; | M + 2F(416, 3.71), 2.17; |
| M + 2F(416, 3.80), 1.33; | M + 3F(434, 3.86), 1.36; | M + 3F(434, 3.93), 1.43; |
| M + O(396, 3.58), 1.35; | M + O(396, 3.74), 0.89; | M + O(396, 3.85), 0.39; |
| M + O + F(414, 3.54), 1.66; | M + O + F(414, 4.14), 1.08; | M + O + F(414, 3.83), 1.54; |
| M + O + F(414, 4.46), 0.96; | M + O + 2F(432, 3.59), 1.62; | M + O + 2F(432, 3.82), 1.4; |
| M + O + 2F(432, 3.90), 1.39; | M + O + 2F(432, 3.96), 1.36; | M + F2(418, 3.50), 1.19; |
| M + F2 + F(436, 3.78), 0.73; | M + 2F2(456, 3.69), 1.23; | M + 2F2 + F(474, 3.80), 0.97; |
| M + 2F2 + F(474, 3.91), 1.19; | M + 2F2 + 2F(492, 3.67), 1.15; | M + 2F2 + 2F(492, 3.84), 1.45; |
| M + 2F2 + 2F(492, 3.96), 1.12; | M + 4F(452, 3.44), 1.49; | M + 4F(452, 3.96), 1.27; |
| M + 4F(452, 4.04), 1.4; | M + 4F(452, 4.97), 1.65; | M + 4F(452, 5.14), 1.82. |

M = donepezil.

The relative metabolic stability of donepezil is defined as 1.00.

Isolation of compounds of interest. General isolation and purification methods can be used by those skilled in the art of compound isolation in medicinal chemistry or natural product chemistry. Specifically the compounds possessing improved properties relative to donepezil can be isolated from the mixture compound library by using HPLC separation. A general procedure for isolating components from non-selective modification of donepezil may be illustrated as below. The mixture may be separated first on an Agilent Eclips column such as 150×4.6 mm type, to be consistent with the analytical LC-MS used in the screening steps (Agilent 1200, Agilent Eclips 150×4.6 mm, gradient elution from 10% acetonitrile/90% 0.1% formic acid in dd-H2O to 90% acetonitrile/10% 0.1% formic acid in dd-H2O, 1 ml/min total flow rate). The mixture after such first separation may produce fractions that contain one particular compound as the major component and some other compounds as minor components. Those fractions that contain a compound of interest (such as the compound having improved properties relative to donepezil) as major components may in turn be further purified by a second HPLC column of different type than Agilent Eclips, such as Supelco Discovery RP Amide C16 column (4.6×250 mm column, gradient 30%-90% MeOH/0.1% formic acid-ddH2O, 1 mL/min flow rate). Often after such second separation, the purity of the desired component will be sufficiently good for structure identification. Else the components of interest can be further separated by an HPLC column of a third type with different column chemistry than the one used in previous separations, such as a fluorine-based column (Thermo PFP Gold, 4.6×250 mm HPLC column, 80% MeOH/0.1% formic acid/20% H2O, isocratic separation, 1 mL/min flow rate). After separation, the compound of interest may be obtained as a major component with purify >95%. Such purified compounds may then be used for structure determination and tested as individual, pure compound to confirm the improved properties over the parent drug donepezil. Drug property tests may include, but not limited to: affinity toward the target protein, metabolic stability using human liver microsome, and biological activity using enzyme assays and cellular activity assays.

Structural determination of compounds purified from the mixture compound library may be done using mass spectrometry and NMR by those skilled in the art of structural determination, see for example: Holzgrabe, U. et al., NMR spectroscopy in drug development and analysis, Wiley-VCH, 1999; Weinheim. Wanner, K. et al., Mass Spectrometry in Medicinal Chemistry: Applications in Drug Discovery, Volume 36, Wiley Interscience 2007; Desiderio, D. M. and Nibbering, N. M. "Mass Spectrometry: Instrumentation, Interpretation, and Applications" Wiley Interscience, 2008, ISBN: 0471713953; McLafferty, F. W. and Tureek, F. "Interpretation of Mass Spectra" 4th edition, University Science Books, 1993. High resolution mass spectrometry measurement may provide information about the formula of the compound. Tandem mass spectrometry (MS/MS) experiments may provide information about the arrangement and connection of atoms and functional groups in the molecule. NMR spectroscopy analysis may also provide the detailed structure information including the arrangement and connection of atoms and functional groups in the molecule. The structure determination of compounds from the mixture compound library is also aided by the available information that the compounds are derived from donepezil through known structural modification reactions.

Enzymatic assay. Acetylcholinesterase inhibitory activity was evaluated at room temperature by the colorimetric method reported by Ellman (Ellman, G. L.; et al. Biochem. Pharmacol. 1961, 7, 88-95). The purified/synthesized compounds or compound mixtures were tested. Assay kit was from Invitrogen. AChE enzyme was from Sigma or prepared from human erythrocyte. Acetylcholine and other reagents and buffers were from Sigma. The assay solution consisted of 0.1 M phosphate buffer pH 8, 0.5 mM 5,5'-dithiobis (2-nitrobenzoic acid) (DTNB, Ellman's reagent), 0.01 unit acetylcholinesterase (Sigma Cat. No. C2888), and 0.5 mM acetylthiocholine iodide (ATCI) as the substrate. Test compounds were added to the assay solution and pre-incubated with the enzyme for 5 min at room temperature before addition of the substrate. The absorbance changes at 410 nm were recorded using a PE EnVision 2104 plate reader. Duplicate sampling was made for each sample. Test compound inhibition to enzyme activity was calculated relative to the positive control without presence of test compound. Negative controls were samples without enzyme.

Pharmacokinetics (PK) measurement. Compound was dozed in 2% DMA and 98% 40% HP-beta-CD in deionized water. A total of 6 male experimental SD rats, approximately 8 weeks of age (180-250 g body weight) were used. For intravenous bolus injection (IV), the animals were placed in a polycarbonate restraint device and dosed via the tail vein. For oral dose (PO), the animals were dosed via oral gavage. Blood samples (300 µL) were collected via retro-orbital puncture after anaesthesia using mixed gas CO2/O2 into tubes containing K3-EDTA anticoagulant at 5 min, 15 min, 0.5, 1, 2, 4, 6, 8, and 24 hours postdose and centrifuged to separate plasma from the samples. The plasma samples were extracted by protein precipitation using 4 volume of CH3CN containing fixed concentration of internal standard compound (IS). The concentrations of analyte in plasma were determined using a high performance liquid chromatography/mass spectrometry (HPLC/MS/MS) method (Shimadzu LC-10ADVP and a Leap autosampler, Thermo Hypersil C18, 50 mm×2.1 mm, Mobile phase A: 0.1% formic acid; B: MeCN, Elution rate: 500 µL/min, Column temperature: 25° C., Injection volume: 10 µL, reverse phase elution from 10% organic to 90% organic in 5 min, Applied Biosystems API3000 triple-quadrupole instrument with a Turbo Ions Spray interface). The data acquisition and data processing were done using Analyst 1.4 software. Standard set of pharmacokinetic parameters including Area Under the Curve (AUC(0-t) and AUC(0-∞), elimination half-live (T½), maximum plasma concentration (Cmax), time to reach maximum plasma concentration (Tmax), clearance (CL), volume of distribution (Vz), and others were calculated.

In vivo evaluation of memory restoring effects of compounds. Evaluation of the compounds of the invention for memory restoring effect using animal models was done by water maze experiment in rats. Restoration of memory was measured by testing compounds on scopolamine-induced impairments of spatial learning and memory. Male Wistar rats (150-170 g) were used. Animals were allowed 1 week acclimation prior to the initiation of the study. All compounds were administered subcutaneously (S.C.). Both test compounds and donepezil were given 30 minutes before scopolamine and scopolamine was given 30 minutes prior to initiation of place acquisition of Moris water maze (MWM) test from day 1 to day 4. No compound was dosed on day 5 on probe trial. Vehicle was 20% hydroxypropyl-beta-cyclodextrin (HP-β-CD). Testing Apparatus is a large circular pool for rats with 160 cm in diameter, 60 cm in height made of plastic and painted black (Mobile Datum information Technology Co., Ltd., Shanghai, China). The pool was filled to a depth of 35 cm of water (maintained at 25° C.+1.0° C.) to cover an invisible (black) 9-cm in diameter round platform. The platform was submerged approximately 1.0 cm below the surface of the water and placed in the center of the northeast quadrant. Four (4) cues attached to the internal wall of the tank: yellow circle, blue square, green triangle and red pentagon. A video monitoring system was used for MWM data collection. Animals were gently placed in the circular tank facing the pool wall and released from four starting points of different quadrants in the maze and allowed to swim in the pool for a maximum of 90 seconds/trial. When the rat reached the platform, it was allowed to remain on it for 30 seconds. If an animal did not escape onto the hidden platform within the 90 seconds then the experimenter gently guided it there by hand. The animals were allowed to remain on the platform for 30 seconds before being returned to the home cage, or a holding cage, for a brief period (5-10 minutes) before the next trial. Animals received a total of 4 trials per day for 4 days. The location of the platform remained the same for all tests except probe trials on day 5. Latencies or the time elapsed and distances traversed to reach the hidden platform were recorded by a video monitoring system. Swim speed was calculated. For the hidden platform test, the latencies and the distances across the four trials for each rat each day were averaged. These results were then analyzed across the four days of testing. The robe trial was carried out on day 5 in the maze where the platform was removed. Although no drug administration applied, animals still received mock treatment before released into the water maze and allowed to swim for 60 seconds twice. The distance swam within the target quadrant, the time spent in the target quadrant and crossing numbers through the position where the platform originally located were determined. See references: R. G. M. Morris, Development of a water-maze procedure for studying spatial learning in the rat, J Neurosci Meth, 1984. 11:47-60; R. K. McNamara and R. W. Skelton, The neuropharmacological and neurochemical basis of place learning in the Morris water maze, Brain Res Rev, 1993. 18:33-49.

Animal toxicological tests. 7-day acute toxicity evaluation was done for selected compounds of this invention on mice and rats. Male and female CD-1 mice (25-30 grams) or SD rats (150-240 grams) were used. The animals were acclimated for 1 week prior to the experiment. The test compounds were dissolved in saline and were dosed orally (PO). Five groups (3 doses plus 1 vehicle and 1 naïve) and 10 mice per group (half male and half female) were used for each compound. All animals were fasted overnight before study. After dosing, animals were placed individually in soft-bedding cages without cage covers. Animal behavioral changes were continuously monitored for 4 hours including autonomic abnormalities (salivation, lacrimation, piloerection, yawning, palpebral closures), neuromuscular abnormalities (posture, gait, fasciculation, convulsions), stereotypical behaviors (sleep, alert, hyper/hypo-activity, slow patterned, fast patterned, restricted, dyskinetic-reactive signs etc.) and lethality. Observations for general health, mortality and moribundity were conducted twice daily after 24 hours. All animals surviving the 7-day observation period were sacrificed by carbon dioxide asphyxiation. Gross necropsies were performed on all animals sacrificed including examinations of main organs and tissue (lung, liver, kidney, heart, intestine, brain).

Exemplary MS or LC-MS Protocol. Samples are analyzed by mass spectrometry alone or by liquid chromatography coupled to mass spectrometry, or other analytical techniques such as NMR, for the quantity and identity of components of the mixture compound libraries described in this method.

Mass spectrometry: Analysis may be performed on, e.g., time-of-flight mass spectrometers LCT (Waters Corporation, Milford, Mass., USA) using a Z-spray (electrospray) ionization source. The electrospray voltage is generally maintained in the range of about 3.5-4.0 kV. Ion optics settings are optimized on the day of the analysis to provide the maximum efficiency of ion to the detector. The effective mass range is generally from m/z 100 to m/z 1000 at a rate of about 1 s/scan.

Liquid chromatography: For example, samples can be introduced through an Agilent1200 (Agilent Technologies, Santa Clara, Calif., USA) chromatography operating in the gradient mode at a flow rate of 1 ml/min. An Eclips C18 base-deactivated column (4.6 mm×150 mm) from Agilent is used for sample separation. The mobile phase gradient is 1-120+ACN 90/10 (v/v) containing 0.1% formic acid to a H2O+ACN 10/90 (v/v) containing 0.1% formic acid in 10 minutes. Samples are introduced through an autosampler as part of the Agilent 1200. The sample injection volumes are generally 1-20 µL.

NMR: 1H NMR and 13C NMR spectra were recorded on Varian Inova 400 or 500 MHz NMR spectrometer. Chemical shifts are given in parts per million (ppm) using tetramethylsilane as the internal standard for spectra obtained in DMSO-d6, CD3OD, and CDCl3.

Compound synthesis. The specific approaches and compounds shown below are not intended to be limiting. The suitability of a chemical group in a compound structure for use in the synthesis of another compound is within the knowledge of one of ordinary skill in the art. Additional methods of synthesizing compounds of Formula I-III and their synthetic precursors, including those within routes not explicitly shown in schemes herein, are within the means of chemists of ordinary skill in the art.

Synthetic chemistry transformations and protecting group methodologies (protection and deprotection) useful in synthesizing the applicable compounds are known in the art and include, for example, those described in Larock R, Comprehensive Organic Transformations, VCH Publishers (1989); Greene T W et al., Protective Groups in Organic Synthesis, 3rd Ed., John Wiley and Sons (1999); Fieser L et al., Fieser and Fieser's Reagents for Organic Synthesis, John Wiley and Sons (1994); and Paquette L, ed., Encyclopedia of Reagents for Organic Synthesis, John Wiley and Sons (1995); Corey, E. J. and Cheng, X.-M., The Logic of Chemical Synthesis, Wiley, New York, 1989, and subsequent editions thereof.

Scheme 1-3 show general routes that may be used to prepare compounds of Formula I-III by those skilled in the art of organic synthesis, $R_a$, $R_b$, $R_c$, $R_d$, and $R_e$ represent any substitution groups at various structural positions of the given molecules that are stable in the shown synthetic step.

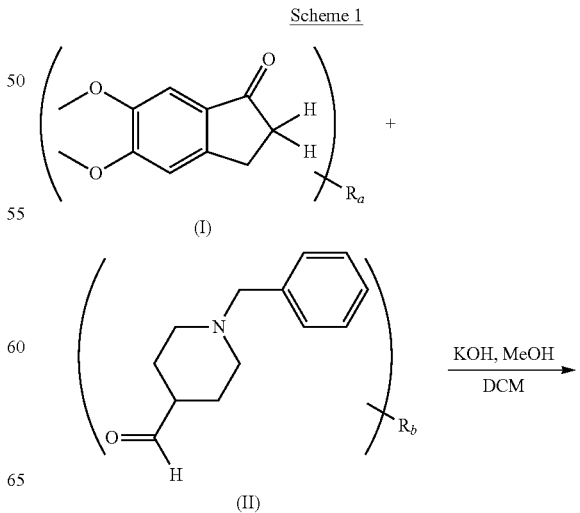

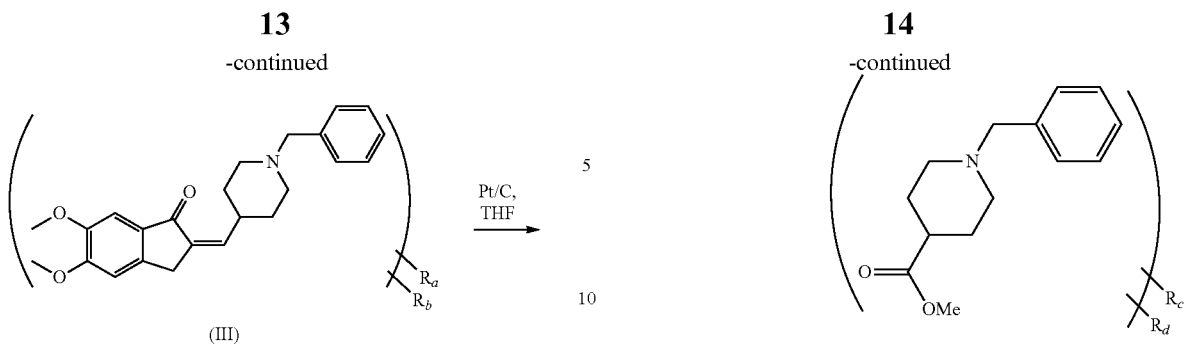

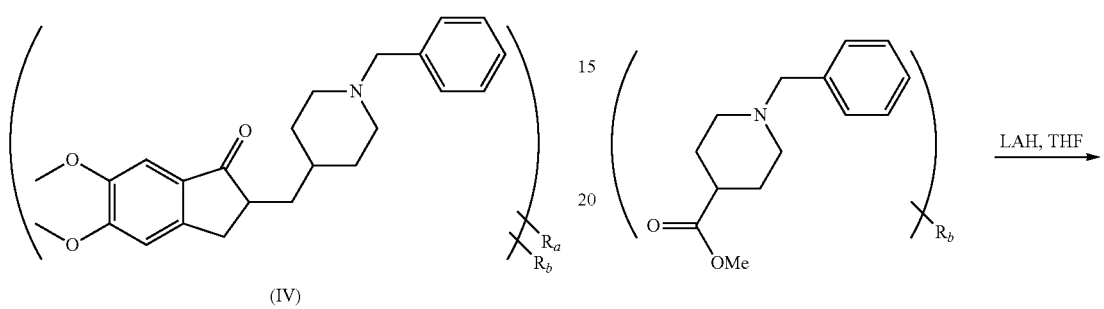

Synthesis of (I) can be carried out as shown in Scheme 2:

Scheme 2

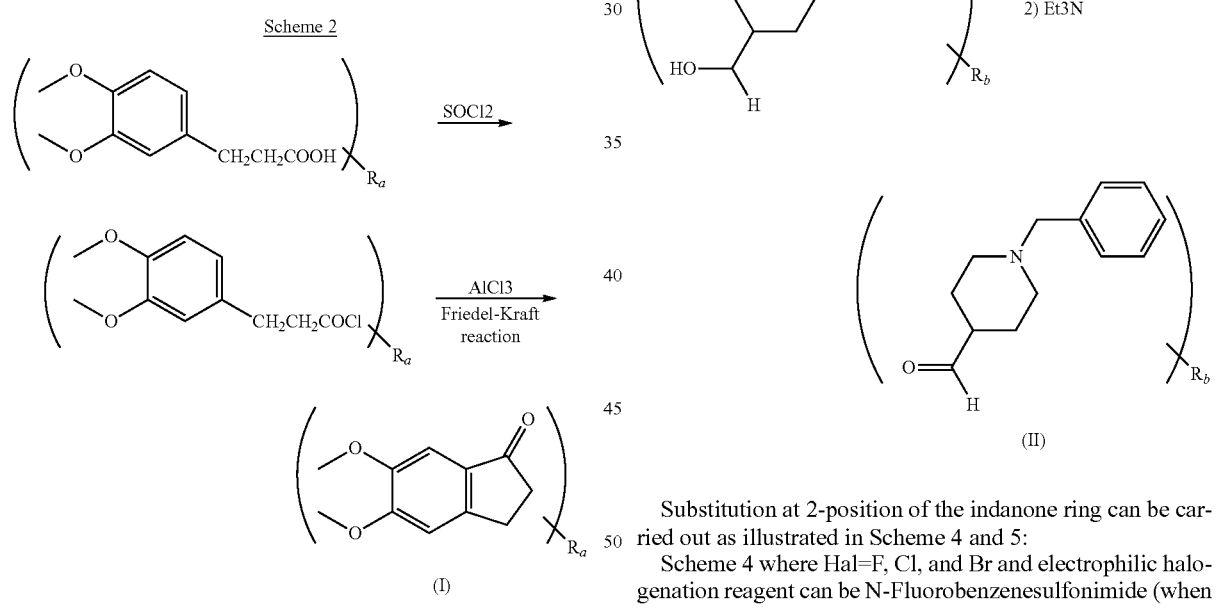

Synthesis of (II) can be carried out as shown in scheme 3:

Scheme 3

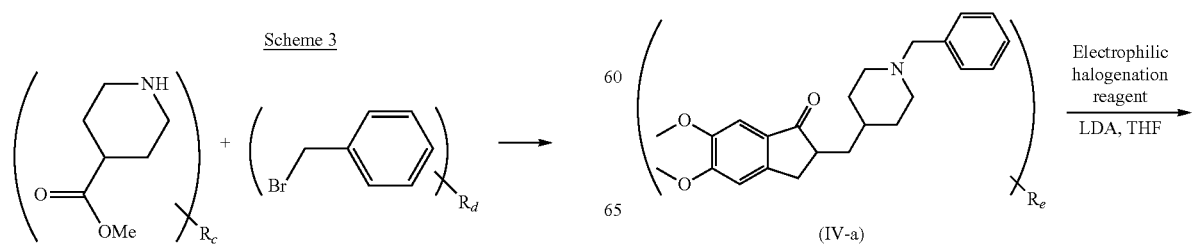

Substitution at 2-position of the indanone ring can be carried out as illustrated in Scheme 4 and 5:

Scheme 4 where Hal=F, Cl, and Br and electrophilic halogenation reagent can be N-Fluorobenzenesulfonimide (when Hal=F), N-chlorosuccinimide (when Hal=Cl), and N-bromosuccinimide or bromine molecule (when Hal=Br).

-continued

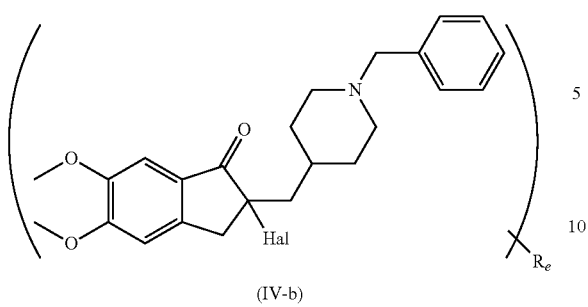

(IV-b)

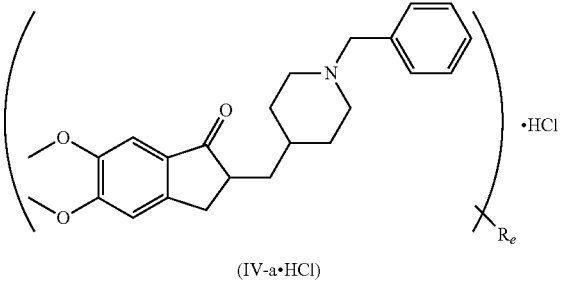

(IV-a·HCl)

Scheme 5 where Nu is a nucleophilic substituent.

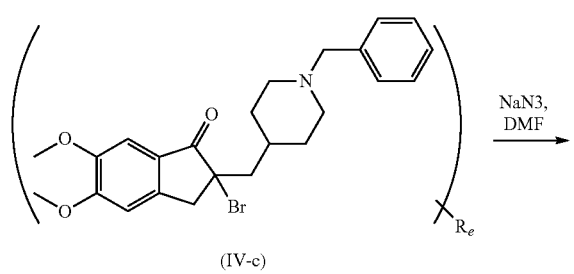

(IV-c)

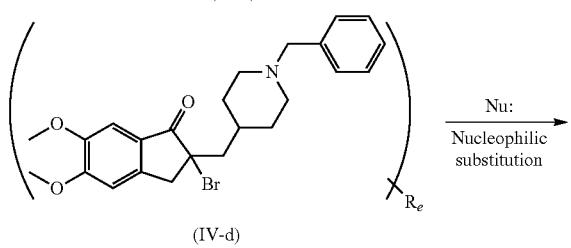

(IV-d)

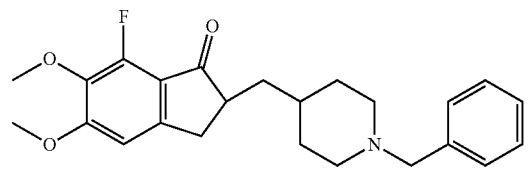 [SMILES: COc1cc2c(c(F)c1OC)C(=O)C(CC1CCN(Cc3ccccc3)CC1)C2]

(IV-e)

Salts of compounds shown above can be prepared by scheme 6.

Scheme 6 where the example used is the hydrochloric acid salt.

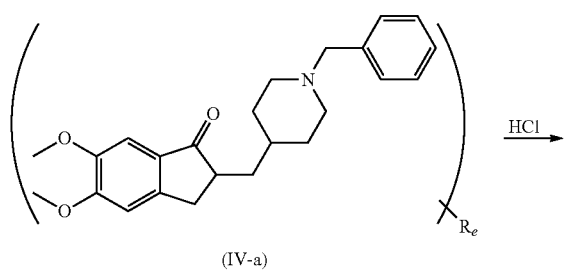

(IV-a)

EXAMPLES

The following examples are offered to illustrate, but not to limit the claims. One of ordinary skill in the art will recognize a variety of non-critical parameters that may be altered without departing from the scope of the claims.

Example 1

2-((1-benzylpiperidin-4-yl)methyl)-7-fluoro-5,6-dimethoxy-2,3-dihydro-1H-inden-1-one (Compound IV-1)

300 mg donepezil was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250×4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material donepezil, were mixed to form the modified donepezil mixture compound library for drug property screening to identify components with improved properties over donepezil. A component with m/z value corresponding to mono-fluorinated donepezil was isolated and purified by successive preparative HPLC separations. The purified compound was analyzed by LC-MS/MS and NMR to provide the structure of the title compound. The observed m/z value 398.2123 (Thermo Finnigan LTQ Orbitrap, positive ion mode), is consistent with calculated m/z of protonated mono-fluorinated donepezil (m/z(calc)=398.2126), molecular formula: C24H29FNO3+. High resolution MSn (n=2-4) experiments on LTQ orbitrap indicate the fluorine substitution is on the phenyl ring of the indanone portion (fragment at m/z 169.0657, calc: 169.0659 for C9H10FO2+). 1H-NMR spectra data indicate the fluorine substitution is at the 7-position of the indanone portion of donepezil. 1H-NMR (500 MHz, CDCl3) δ ppm 1.3-1.9 (m, 7H), 2.3-2.8 (m, 5H), 3.0 (dd, J=17, 5 Hz, 1H), 3.2 (m, 1H), 3.6 (s, 2H), 3.9 (s, 3H), 3.95 (s, 3H), 6.7 (s, 1H, 4-indanone), 7.30 (m, 5H). Synthesis by Scheme 5 produced >95% purity compound, mass spec analysis: positive ion m/z 398.2122 (calc 398.2126). 1H-NMR (500 MHz, CDCl3) δ ppm 1.3-1.9 (m, 7H), 2.3-2.8 (m, 5H), 3.0 (dd, J=17, 5 Hz, 1H), 3.2 (m, 1H), 3.6 (s, 2H), 3.9 (s, 3H), 3.95 (s, 3H), 6.7 (s, 1H, 4-indanone), 7.30 (m, 5H).

Example 2

2-((1-benzylpiperidin-4-yl)methyl)-4,7-difluoro-5,6-dimethoxy-2,3-dihydro-1H-inden-1-one (Compound IV-2)

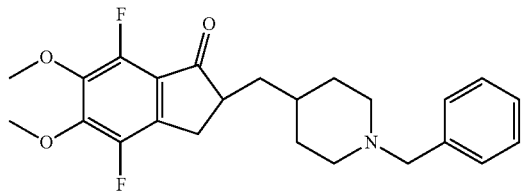 [SMILES: COc1c(F)c2c(c(F)c1OC)C(=O)C(CC1CCN(Cc3ccccc3)CC1)C2]

300 mg donepezil was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250×4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material donepezil, were mixed to form the modified donepezil mixture compound library for drug property screening to identify components with improved properties over donepezil. A component with m/z value corresponding to di-fluorinated donepezil was isolated and purified by successive preparative HPLC separations. The purified compound was analyzed by LC-MS/MS and NMR to provide the structure of the title compound. The observed m/z value 416.2029 (Thermo Finnigan LTQ Orbitrap, positive ion mode), is consistent with calculated m/z of protonated di-fluorinated donepezil (m/z(calc)=416.2032), molecular formula: C24H28F2NO3+. High resolution MSn (n=2-4) experiments on LTQ orbitrap indicate both fluorine substitutions are on the phenyl ring of the indanone portion of donepezil (fragment at m/z 187.0562, calc: 187.0565 for C9H9F2O2+). 1H-NMR spectra data indicate the two fluorine substitutions are at the 4- and 7-position of the indanone portion of donepezil (both 4- and 7-indanone proton signals disappeared). 1H-NMR (500 MHz, CDCl3) δ ppm 1.3-1.9 (m, 7H), 2.3-2.8 (m, 5H), 3.1 (dd, J=17, 5 Hz, 1H), 3.2 (m, 1H), 3.6 (s, 2H), 3.91 (s, 3H), 3.96 (s, 3H), 7.30 (m, 5H). Synthesis by Scheme 5 produced >95% purity compound, mass spec analysis: positive ion m/z 416.2028 (calc 416.2032). 1H-NMR (500 MHz, CDCl3) δ ppm 1.3-1.9 (m, 7H), 2.3-2.8 (m, 5H), 3.1 (dd, J=17, 5 Hz, 1H), 3.2 (m, 1H), 3.6 (s, 2H), 3.91 (s, 3H), 3.96 (s, 3H), 7.30 (m, 5H).

Example 3

2-((1-(4-fluorobenzyl)piperidin-4-yl)methyl)-5,6-dimethoxy-2,3-dihydro-1H-inden-1-one (Compound IV-3)

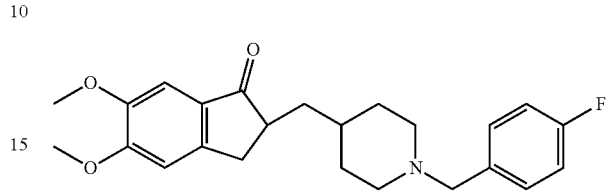

300 mg donepezil was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250×4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material donepezil, were mixed to form the modified donepezil mixture compound library for drug property screening to identify components with improved properties over donepezil. A component with m/z value corresponding to mono-fluorinated donepezil was isolated and purified by successive preparative HPLC separations. The purified compound was analyzed by LC-MS/MS and NMR to provide the structure of the title compound. The observed m/z value 398.2123 (Thermo Finnigan LTQ Orbitrap, positive ion mode), is consistent with calculated m/z of protonated mono-fluorinated donepezil (m/z(calc)=398.2126), molecular formula: C24H29FNO3+. High resolution MSn (n=2-4) experiments on LTQ orbitrap indicate the fluorine substitution is on the benzyl ring of donepezil (fragment at m/z 190.1024, calc: 190.1027 for C12H13FN+). 1H-NMR data indicates fluorine substitution is at the 4-position of the benzyl ring. 1H-NMR (500 MHz, CDCl3) δ ppm 1.3-1.9 (m, 7H), 2.3-2.8 (m, 5H), 3.0 (dd, J=17, 5 Hz, 1H), 3.2 (m, 1H), 3.6 (s, 2H), 3.9 (s, 3H), 3.95 (s, 3H), 6.70 (s, 1H, 4-indanone), 7.20 (s, 1H, 7-indanone), 7.20 (m, 2H), 7.40 (in, 2H). Synthesis by Scheme 5 produced >95% purity compound, mass spec analysis: positive ion m/z 398.2123 (calc 398.2126). 1H-NMR (500 MHz, CDCl3) δ ppm 1.3-1.9 (m, 7H), 2.3-2.8 (m, 5H), 3.0 (dd, J=17, 5 Hz, 1H), 3.2 (m, 1H), 3.6 (s, 2H), 3.9 (s, 3H), 3.95 (s, 3H), 6.70 (s, 1H, 4-indanone), 7.20 (s, 1H, 7-indanone), 7.20 (m, 2H), 7.40 (in, 2H).

Example 4

2-((1-benzyl-4-fluoropiperidin-4-yl)methyl)-5,6-dimethoxy-2,3-dihydro-1H-inden-1-one (Compound IV-4)

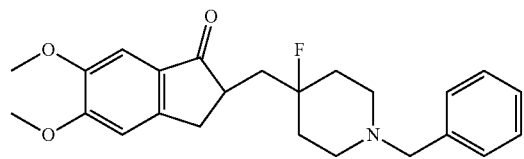 [SMILES: COc1cc2c(cc1OC)C(=O)C(CC1(F)CCN(Cc3ccccc3)CC1)C2]

300 mg donepezil was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250×4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material donepezil, were mixed to form the modified donepezil mixture compound library for drug property screening to identify components with improved properties over donepezil. A component with m/z value corresponding to mono-fluorinated donepezil was isolated and purified by successive preparative HPLC separations. The purified compound was analyzed by LC-MS/MS and NMR to provide the structure of the title compound. The observed m/z value 398.2122 (Thermo Finnigan LTQ Orbitrap, positive ion mode), is consistent with calculated m/z of protonated mono-fluorinated donepezil (m/z(calc)=398.2126), molecular formula: C24H29FNO3+. High resolution MSn (n=2-4) experiments on LTQ orbitrap indicate the fluorine substitution is on the piperidine ring of donepezil (fragments at m/z 189.0910 (indanone-H2O) and 91.0480 (benzyl) indicate the fluorine atom is not on the indanone and not on the benzyl portion of the molecule). 1H-NMR spectra data indicate the fluorine substitution is at the 4-position of the piperidine ring of donepezil. 1H-NMR (500 MHz, CDCl3) δ ppm 1.6-1.8 (m, 4H), 1.96 (m, 1H), 2.34 (m, 3H), 2.72 (m, 2H), 2.82 (m, 1H), 2.89 (dd, J=18, 4 Hz, 1H), 3.33 (dd, J=18, 7 Hz, 1H), 3.54 (s, 2H), 3.91 (s, 3H), 3.96 (s, 3H), 6.86 (s, 1H, 4-indanone), 7.18 (s, 1H, 7-indanone), 7.30 (m, 5H). Synthesis by Scheme 5 produced >95% purity compound, mass spec analysis: positive ion m/z 398.2121 (calc 398.2126). 1H-NMR (500 MHz, CDCl3) δ ppm 1.6-1.8 (m, 4H), 1.96 (m, 1H), 2.34 (m, 3H), 2.72 (m, 2H), 2.82 (m, 1H), 2.89 (dd, J=18, 4 Hz, 1H), 3.33 (dd, J=18, 7 Hz, 1H), 3.54 (s, 2H), 3.91 (s, 3H), 3.96 (s, 3H), 6.86 (s, 1H, 4-indanone), 7.18 (s, 1H, 7-indanone), 7.30 (m, 5H).

Example 5

2-((1-(3-chlorobenzyl)piperidin-4-yl)methyl)-2-fluoro-5,6-dimethoxy-2,3-dihydro-1H-inden-1-one (Compound IV-5)

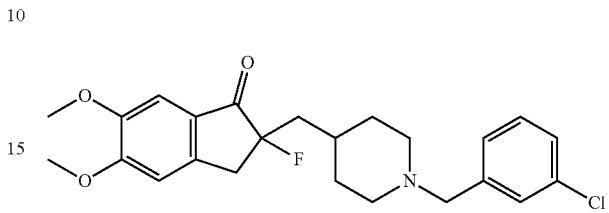

300 mg donepezil was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250×4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material donepezil, were mixed to form the modified donepezil mixture compound library for drug property screening to identify components with improved properties over donepezil. A component with m/z value corresponding to substitution by a fluorine and a chlorine atoms of donepezil was isolated and purified by successive preparative HPLC separations. The purified compound was analyzed by LC-MS/MS and NMR to provide the structure of the title compound. The observed m/z value 432.1731 (Thermo Finnigan LTQ Orbitrap, positive ion mode), is consistent with calculated m/z of protonated donepezil with one F and one Cl substitution (m/z(calc)=432.1736), molecular formula: C24H28ClFNO3+, High resolution MSn. (n=2-4) experiments on LTQ orbitrap indicate Cl is on the benzyl ring and fluorine substitutions is not on the benzyl ring side of donepezil (fragment at m/z 125.0150 and 127.0120 indicates the Cl atom is on the benzyl ring, C7H6Cl+). 1H-NMR spectra data indicate the fluorine substitution is at the 2-position of the indanone ring and the Cl atom is at the 3-position of the benzyl ring of donepezil. 1H-NMR (500 MHz, CDCl3) δ ppm 1.3-1.9 (m, 5H), 2.1-2.7 (m, 6H), 3.3 (dd, J=17, 14 Hz, 1H), 3.5 (s, 2H), 3.7 (dd, J=17, 14 Hz, 1H), 3.9 (s, 3H), 4.0 (s, 3H), 6.9 (s, 1H), 7.1 (s, 1H), 7.2 (s, 1H), 7.30 (m, 3H). Synthesis by Scheme 5 produced >95% purity compound, mass spec analysis: positive ion m/z 432.1732/434.1705 (calc 432.1736/434.1707). 1H-NMR (500 MHz, CDCl3) δ ppm 1.3-1.9 (m, 5H), 2.1-2.7 (m, 6H), 3.3 (dd, J=17, 14 Hz, 1H), 3.5 (s, 2H), 3.7 (dd, J=17, 14 Hz, 1H), 3.9 (s, 3H), 4.0 (s, 3H), 6.9 (s, 1H), 7.1 (s, 1H), 7.2 (s, 1H), 7.30 (m, 3H).

Example 6

2-((1-benzylpiperidin-4-yl)methyl)-7-chloro-2-fluoro-5,6-dimethoxy-2,3-dihydro-1H-inden-1-one (Compound IV-6)

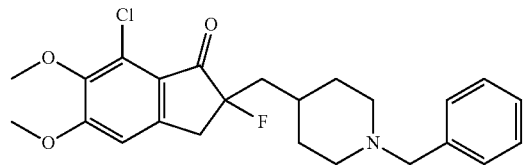 [SMILES: COc1cc2c(c(Cl)c1OC)C(=O)C(F)(CC1CCN(Cc3ccccc3)CC1)C2]

300 mg donepezil was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250×4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material donepezil, were mixed to form the modified donepezil mixture compound library for drug property screening to identify components with improved properties over donepezil. A component with m/z value corresponding to substitution by one fluorine and one chlorine of donepezil was isolated and purified by successive preparative HPLC separations. The purified compound was analyzed by LC-MS/MS and NMR to provide the structure of the title compound. The observed m/z value 432.1729 (Thermo Finnigan LTQ Orbitrap, positive ion mode), is consistent with calculated m/z of protonated donepezil with one fluorine and one chlorine substitution (m/z(calc)=432.1736), molecular formula: C24H28ClFNO3+. High resolution MSn (n 2-4) experiments on LTQ orbitrap indicate both fluorine and Cl substitutions are on the indanone ring side of donepezil (fragment at m/z 185.0362/187.0330, calc: 185.0364/187.0335 for C9H10ClO2+ indicates the indanone ring is substituted with Cl, fragment at m/z 91.0479 indicates benzyl without substitution, C7H7+). 1H-NMR spectra data indicate F-substitutions is at the 2-position and Cl-substitution is at the 7-position of the indanone ring of donepezil. 1H-NMR (500 MHz, CDCl3) δ ppm 1.3-1.8 (m, 5H), 2.1-2.8 (m, 6H), 3.3 (dd, J=17, 14 Hz, 1H), 3.5 (s, 2H), 3.7 (dd. J=17, 14 Hz, 1H), 3.9 (s, 3H), 4.0 (s, 3H), 6.8 (s, 1H, 4-indanone), 7.30 (m, 5H). Synthesis by Scheme 5 produced >95% purity compound, mass spec analysis: positive ion m/z 432.1733/434.1702 (calc 432.1736/434.1707), 1H-NMR (500 MHz, CDCl3) δ ppm 1.3-1.8 (m, 5H), 2.1-2.8 (m, 6H), 3.3 (dd, J=17, 14 Hz, 1H), 3.5 (s, 2H), 3.7 (dd, J=17, 14 Hz, 1H), 3.9 (s, 3H), 4.0 (s, 3H), 6.8 (s, 1H, 4-indanone), 7.30 (m, 5H).

Example 7

2-((1-benzylpiperidin-4-yl)methyl)-2-chloro-4-fluoro-5,6-dimethoxy-2,3-dihydro-1H-inden-1-one (Compound IV-7)

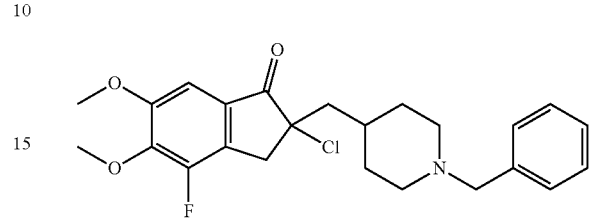

300 mg donepezil was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250×4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material donepezil, were mixed to form the modified donepezil mixture compound library for drug property screening to identify components with improved properties over donepezil. A component with m/z value corresponding to substitution by one fluorine and one chlorine of donepezil was isolated and purified by successive preparative HPLC separations. The purified compound was analyzed by LC-MS/MS and NMR to provide the structure of the title compound. The observed m/z value 432.1731 (Thermo Finnigan LTQ Orbitrap, positive ion mode), is consistent with calculated m/z of protonated donepezil with one fluorine and one chlorine substitution (m/z(calc)=432.1736), molecular formula: C24H28ClFNO3+. High resolution MSn (n=2-4) experiments on LTQ orbitrap indicate both substitutions are on the indanone ring side of donepezil (F-substitution is on phenyl ring of indanone: fragment at m/z 169.0656, calc: 169.0659 for C9H10FO2+, fragment at m/z 91.0481 indicates the benzyl ring is not substituted). 1H-NMR spectra data indicate the nature of the substitutions is 2-Cl and 4-F of the indanone ring of donepezil. 1H-NMR (500 MHz, CDCl3) δ ppm 1.3-1.8 (m, 5H), 2.0-2.8 (m, 6H), 3.3 (d, J=5 Hz, 1H), 3.5 (s, 2H), 3.8 (d, J=5 Hz, 1H), 3.9 (s, 3H), 4.0 (s, 3H), 7.1 (s, 1H, 7-indanone), 7.30 (m, 5H). Synthesis by Scheme 5 produced >95% purity compound, mass spec analysis: positive ion m/z 432.1735/434.1703 (calc 432.1736/434.1707). 1H-NMR (500 MHz, CDCl3) δ ppm 1.3-1.8 (m, 5H), 2.0-2.8 (m, 6H), 3.3 (d, J=15 Hz, 1H), 3.5 (s, 2H), 3.8 (d, J=15 Hz, 1H), 3.9 (s, 3H), 4.0 (s, 3H), 7.1 (s, 1H, 7-indanone), 730 (m, 5H).

Example 8

2-((1-benzyl-4-fluoropiperidin-4-yl)methyl)-2-fluoro-5,6-dimethoxy-2,3-dihydro-1H-inden-1-one (Compound IV-8)

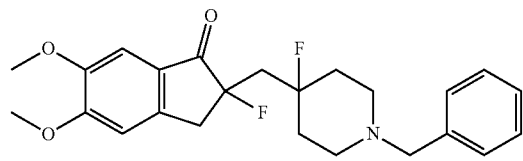 [SMILES: COc1cc2c(cc1OC)C(=O)C(F)(CC1(F)CCN(Cc3ccccc3)CC1)C2]

300 mg donepezil was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250×4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material donepezil, were mixed to form the modified donepezil mixture compound library for drug property screening to identify components with improved properties over donepezil. A component with m/z value corresponding to di-fluorinated donepezil was isolated and purified by successive preparative HPLC separations. The purified compound was analyzed by LC-MS/MS and NMR to provide the structure of the title compound. The observed m/z value 416.2027 (Thermo Finnigan LTQ Orbitrap, positive ion mode), is consistent with calculated m/z of protonated di-fluorinated donepezil (m/z(calc)=416.2032), molecular formula: C24H28F2NO3+. High resolution MSn (n=2-4) experiments on LTQ orbitrap indicate fluorine substitutions are not on the benzyl ring of donepezil (fragment at m/z 91.0547, calc: 91.0548 for C7H7+ indicates the benzyl ring is not substituted), also not on the phenyl ring of indanone (fragment at m/z 151.0750, calc: 151.0754 for C9H11O2+). 1H-NMR spectra data indicate the fluorine substitutions are at the 2-position of the indanone ring and 4-position of the piperidine ring of donepezil. 1H-NMR (500 MHz, CDCl3) δ ppm 1.7-2.2 (m, 5H), 2.3-2.5 (m, 3H), 2.7 (m, 2H), 3.28 (dd, J=18, 15, 1H), 3.52 (dd, J=18, 12, 2H), 3.75 (dd, J=17, 15, 1H), 3.91 (s, 3H), 3.98 (s, 3H), 6.84 (s, 1H, 4-indanone), 7.20 (s, 1H, 7-indanone), 7.30 (m, 5H). Synthesis by Scheme 5 produced >95% purity compound, mass spec analysis: positive ion m/z 416.2028 (calc 416.2032). 1H-NMR (500 MHz, CDCl3) δ ppm 1.7-2.2 (m, 5H), 2.3-2.5 (m, 3H), 2.7 (m, 2H), 3.28 (dd, J=18, 15, 1H), 3.52 (dd, J=18, 12, 2H), 3.75 (dd, J=17, 15, 1H), 3.91 (s, 3H), 3.98 (s, 3H), 6.84 (s, 1H, 4-indanone), 7.20 (s, 1H, 7-indanone), 7.30 (m, 5H).

Example 9

2-((1-benzyl-4-fluoropiperidin-4-yl)methyl)-2,7-difluoro-5,6-dimethoxy-2,3-dihydro-1H-inden-1-one (Compound IV-9)

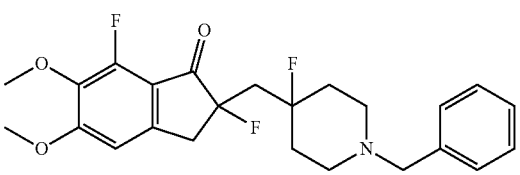 [SMILES: COc1cc2c(c(F)c1OC)C(=O)C(F)(CC1(F)CCN(Cc3ccccc3)CC1)C2]

300 mg donepezil was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250×4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material donepezil, were mixed to form the modified donepezil mixture compound library for drug property screening to identify components with improved properties over donepezil. A component with m/z value corresponding to tri-fluorinated donepezil was isolated and purified by successive preparative HPLC separations. The purified compound was analyzed by LC-MS/MS and NMR to provide the structure of the title compound. The observed m/z value 434.1931 (Thermo Finnigan LTQ Orbitrap, positive ion mode), is consistent with calculated m/z of protonated tri-fluorinated donepezil (m/z(calc)=434.1938), molecular formula: C24H27F3NO3+. High resolution MSn (n=2-4) experiments on LTQ orbitrap indicate one fluorine substitution is on the phenyl ring of indanone while none is on the benzyl ring (fragment at m/z 91.0545 indicates the benzyl ring is not substituted). 1H-NMR spectra data indicate the fluorine substitutions are at the 2- and 7-positions of the indanone ring, and 4-position of the piperidine ring of donepezil. 1H-NMR (500 MHz, CDCl3) δ ppm 1.7-2.6 (m, 10H), 3.3 (dd, J=17, 15 Hz, 1H), 3.6 (s, 2H), 3.8 (dd, J=17, 15 Hz, 1H), 3.90 (s, 3H), 4.0 (s, 3H), 6.70 (s, 1H, 4-indanone), 7.30 (m, 5H). Synthesis by Scheme 5 produced >95% purity compound, mass spec analysis positive ion m/z 434.1934 (calc 434.1938). 1H-NMR (500 MHz, CDCl3) δ ppm 1.7-2.6 (m, 10H), 3.3 (dd, J=17, 15 Hz, 1H), 3.6 (s, 2H), 3.8 (dd, J=17, 15 Hz, 1H), 3.90 (s, 3H), 4.0 (s, 3H), 6.70 (s, 1H, 4-indanone), 7.30 (m, 5H).

Example 10

2-((1-(4-chlorobenzyl)piperidin-4-yl)methyl)-2,7-difluoro-5,6-dimethoxy-2,3-dihydro-1H-inden-1-one (Compound IV-10)

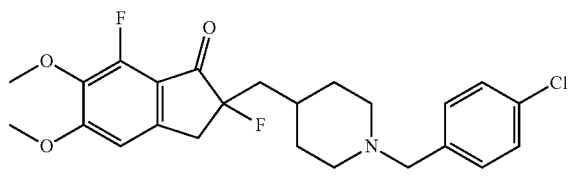 [SMILES: COc1cc2c(c(F)c1OC)C(=O)C(F)(CC1CCN(Cc3ccc(Cl)cc3)CC1)C2]

300 mg donepezil was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250×4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material donepezil, were mixed to form the modified donepezil mixture compound library for drug property screening to identify components with improved properties over donepezil. A component with m/z value corresponding to substitutions by two fluorine and one chlorine atoms of donepezil was isolated and purified by successive preparative HPLC separations. The purified compound was analyzed by LC-MS/MS and NMR to provide the structure of the title compound. The observed m/z value 450.1639 (Thermo Finnigan LTQ Orbitrap, positive ion mode), is consistent with calculated m/z of protonated donepezil with substitution by two fluorine and one chlorine (m/z(calc)=450.1642), molecular formula: C24H27ClF2NO3+. High resolution MSn (n=2-4) experiments on LTQ orbitrap indicate the chlorine substitution is on the benzyl ring (fragment at m/z 125.0151 and 127.0120 indicates the benzyl ring is chlorinated), one fluorine substitution is on the indanone ring of donepezil (fragment at m/z 169.0655, calc: 169.0659 for C9H10FO2+). 1H-NMR spectra data indicate the chlorine substitution is at the 4-position of the benzyl ring, and the fluorine substitutions are at 2- and 7-positions of indanone. 1H-NMR (500 MHz, CDCl3) δ ppm 1.3-1.8 (m, 5H), 2.1-2.8 (m, 6H), 3.3 (dd, J=17, 15 Hz, 1H), 3.6 (s, 2H), 3.8 (dd, J=17, 15 Hz, 1H), 3.9 (s, 3H), 4.0 (s, 3H), 6.7 (s, 1H, 4-indanone), 7.30 (m, 4H). Synthesis by Scheme 5 produced >95% purity compound, mass spec analysis: positive ion m/z 450.1640 (calc 450.1642). 1H-NMR (500 MHz, CDCl3) δ ppm 1.3-1.8 (m, 5H), 2.1-2.8 (m, 6H), 3.3 (dd, J=17, 15 Hz, 1H), 3.6 (s, 2H), 3.8 (dd, J=17, 15 Hz, 1H), 3.9 (s, 3H), 4.0 (s, 3H), 6.7 (s, 1H, 4-indanone), 7.30 (m, 4H).

Example 11

2-fluoro-2-((4-fluoro-1-(4-fluorobenzyl)piperidin-4-yl)methyl)-5,6-dimethoxy-2,3-dihydro-1H-inden-1-one (Compound IV-11)

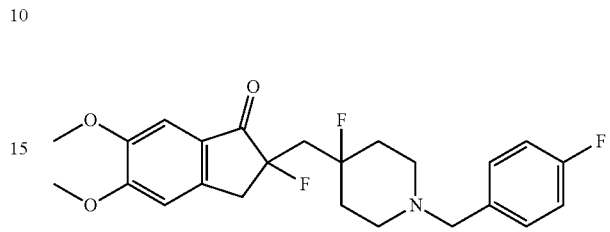

300 mg donepezil was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250×4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material donepezil, were mixed to form the modified donepezil mixture compound library for drug property screening to identify components with improved properties over donepezil. A component with m/z value corresponding to tri-fluorinated donepezil was isolated and purified by successive preparative HPLC separations. The purified compound was analyzed by LC-MS/MS and NMR to provide the structure of the title compound. The observed m/z value 434.1931 (Thermo Finnigan LTQ Orbitrap, positive ion mode), is consistent with calculated m/z of protonated tri-fluorinated donepezil (m/z(calc)=434.1938), molecular formula: C24H27F3NO3+. High resolution MSn (n=2-4) experiments on LTQ orbitrap indicate one fluorine substitution is at the benzyl ring (fragment at m/z 190.1023, calc: 190.1027 for C12H13FN+) while the phenyl ring of indanone is not substituted (m/z 151.0752 for C9H11O2+). 1H-NMR spectra data indicate the fluorine substitutions are at the 2-position of the indanone ring, 4-position of the piperidine ring and 4-position of the benzyl ring of donepezil. 1H-NMR (500 MHz, CDCl3) δ ppm 1.8-22.4 (m, 6H), 2.5-2.9 (m, 4H), 3.3 (dd, J=17, 15 Hz, 1H), 3.6 (m, 3H), 3.9 (s, 3H), 4.0 (s, 3H), 6.9 (s, 1H, 4-indanone), 7.1 (s, 1H, 7-indanone), 7.20 (m, 2H), 7.30 (m, 2H). Synthesis by Scheme 5 produced >95% purity compound, mass spec analysis: positive ion m/z 434.1935 (calc m/z 434.1938). 1H-NMR (500 MHz, CDCl3) δ ppm 1.8-22.4 (m, 6H), 2.5-2.9 (m, 4H), 3.3 (dd, J=17, 15 Hz, 1H), 3.6 (m, 3H), 3.9 (s, 3H), 4.0 (s, 3H), 6.9 (s, 1H, 4-indanone), 7.1 (s, 1H, 7-indanone), 7.20 (m, 2H), 7.30 (m, 2H).

Example 12

2,7-difluoro-2-((1-(4-hydroxybenzyl)piperidin-4-yl)methyl)-5,6-dimethoxy-2,3-dihydro-1H-inden-1-one (Compound IV-12)

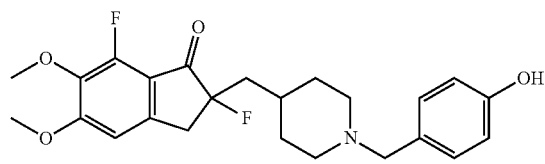 [SMILES: COc1cc2c(c(F)c1OC)C(=O)C(F)(CC1CCN(Cc3ccc(O)cc3)CC1)C2]

300 mg donepezil was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax CS 250×4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material donepezil, were mixed to form the modified donepezil mixture compound library for drug property screening to identify components with improved properties over donepezil. A component with m/z value corresponding to substitution of donepezil by two fluorine and addition of one oxygen atoms was isolated and purified by successive preparative HPLC separations. The purified compound was analyzed by LC-MS/MS and NMR to provide the structure of the title compound. The observed m/z value 432.1973 (Thermo Finnigan LTQ Orbitrap, positive ion mode), is consistent with calculated m/z of protonated donepezil with two fluorine and one oxygen atoms substitution (m/z(calc)=432.1981), molecular formula: C24H28F2NO4+. High resolution MSn (n=2-4) experiments on LTQ orbitrap indicate oxygen substitution is on the benzyl ring (fragment at m/z 107.0488, calc: 107.0491 for C7H7O+, likely a hydroxyl group substitution) and one fluorine substitution is on the phenyl ring of indanone (fragment at m/z 169.0655, calc: 169.0659 for C9H10FO2+). 1H-NMR spectra data indicate the hydroxyl substitution is at the 4-position of the benzyl ring and fluorine substitutions are at 2- and 7-position of the indanone ring of donepezil. 1H-NMR (500 MHz, CDCl3) δ ppm 1.3-1.8 (m, 5H), 2.1-2.8 (m, 6H), 3.3 (dd, J=17, 15 Hz, 1H), 3.6 (s, 2H), 3.8 (dd, J=17, 15 Hz, 1H), 3.9 (s, 3H), 4.0 (s, 3H), 6.7 (m, 5H), 7.20 (m, 2H). Synthesis by Scheme 5 produced >95% purity compound, mass spec analysis: positive ion m/z 432.1975 (calc 432.1981). 1H-NMR (500 MHz, CDCl3) δ ppm 1.3-1.8 (m, 5H), 2.1-2.8 (m, 6H), 3.3 (dd, J=17, 15 Hz, 1H), 3.6 (s, 2H), 3.8 (dd, J=17, 15 Hz, 1H), 3.9 (s, 3H), 4.0 (s, 3H), 6.7 (m, 5H), 7.20 (in, 2H).

Example 13

2-((1-benzyl-4-fluoropiperidin-4-yl)methyl)-7-fluoro-5,6-dimethoxy-2,3-dihydro-1H-inden-1-one (Compound IV-13)

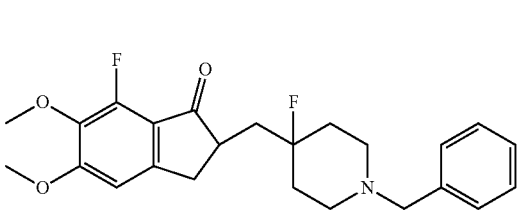 [SMILES: COc1cc2c(c(F)c1OC)C(=O)C(CC1(F)CCN(Cc3ccccc3)CC1)C2]

300 mg donepezil was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250×4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material donepezil, were mixed to form the modified donepezil mixture compound library for drug property screening to identify components with improved properties over donepezil. A component with m/z value corresponding to di-fluorinated donepezil was isolated and purified by successive preparative HPLC separations. The purified compound was analyzed by LC-MS/MS and NMR to provide the structure of the title compound. The observed m/z value 416.2031 (Thermo Finnigan LTQ Orbitrap, positive ion mode), is consistent with calculated m/z of protonated di-fluorinated donepezil (m/z(calc)=416.2032), molecular formula: C24H28F2NO3+. High resolution MSn (n=2-4) experiments on LTQ orbitrap indicate one fluorine substitutions is on the phenyl ring of indanone (fragment at m/z 169.0657, calc: 169.0659 for C9H10FO2+). 1H-NMR spectra data indicate the fluorine substitutions are at the 7-position of indanone ring and 4-position of the piperidine ring of donepezil. 1H-NMR (500 MHz, CDCl3) δ ppm 1.7-2.2 (m, 6H), 2.5-2.8 (m, 4H), 3.0 (dd, J=18, 4 Hz, 1H), 3.2 (dd, J=18, 7 Hz, 1H), 3.4 (m, 1H), 3.6 (s, 2H), 3.91 (s, 3H), 3.98 (s, 3H), 6.7 (s, 1H, 4-indanone), 7.30 (m, 5H). Synthesis by Scheme 5 produced >95% purity compound, mass spec analysis: positive ion m/z 416.2031 (calc 416.2032). 1H-NMR (500 MHz, CDCl3) δ ppm 1.7-2.2 (m, 6H), 2.5-2.8 (m, 4H), 3.0 (dd, J=18, 4 Hz, 1H), 3.2 (dd, J=18, 7 Hz, 1H), 3.4 (m, 1H), 3.6 (s, 2H), 3.91 (s, 3H), 3.98 (s, 3H), 6.7 (s, 1H, 4-indanone), 7.30 (m, 5H).

Example 14

4-fluoro-2-((1-(4-fluorobenzyl)piperidin-4-yl)methyl)-5,6-dimethoxy-2,3-dihydro-H-inden-1-one (Compound IV-14)

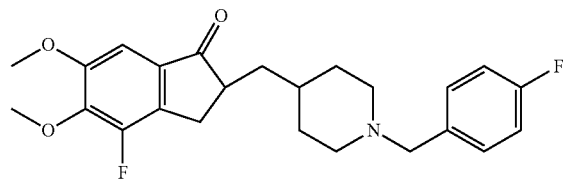 [SMILES: COc1cc2c(c(F)c1OC)CC(CC1CCN(Cc3ccc(F)cc3)CC1)C2=O]

300 mg donepezil was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250×4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material donepezil, were mixed to form the modified donepezil mixture compound library for drug property screening to identify components with improved properties over donepezil. A component with m/z value corresponding to di-fluorinated donepezil was isolated and purified by successive preparative HPLC separations. The purified compound was analyzed by LC-MS/MS and NMR to provide the structure of the title compound. The observed m/z value 416.2031 (Thermo Finnigan LTQ Orbitrap, positive ion mode), is consistent with calculated m/z of protonated donepezil with di-fluorination (m/z(calc)=416.2032), molecular formula: C24H28F2NO3+. High resolution MSn (n=2-4) experiments on LTQ orbitrap indicate one fluorine is on the phenyl ring of indanone and another fluorine is on the benzyl ring of donepezil (fragment at m/z 169.0655, calc: 169.0659 for C9H10FO2+, and fragment at m/z 190.1026, calc: 190.1027 for C12H13FN+). 1H-NMR spectra data indicate the fluorine substitutions are at 4-position of the indanone ring and 4-position of the benzyl ring of donepezil. 1H-NMR (500 MHz, CDCl3) δ ppm 1.3-1.8 (m, 7H), 2.3-2.9 (m, 5H), 3.1 (m, 2H), 3.6 (s, 2H), 3.9 (s, 3H), 3.95 (s, 3H), 7.1 (s, 1H, 7-indanone), 7.20 (m, 2H), 7.40 (in, 2H). Synthesis by Scheme 5 produced >95% purity compound, mass spec analysis: positive ion m/z 416.2025 (calc 416.2032). 1H-NMR (500 MHz, CDCl3) δ ppm 1.3-1.8 (m, 7H), 2.3-2.9 (m, 5H), 3.1 (m, 2H), 3.6 (s, 2H), 3.9 (s, 3H), 3.95 (s, 3H), 7.1 (s, 1H, 7-indanone), 7.20 (m, 2H), 7.40 (m, 2H).

Example 15

Compound Synthesis

The synthesis of the compounds of this invention can be accomplished according to Scheme 1-4 in general by those skilled in the art of organic synthesis. Similar procedures can be used to synthesize other compounds claimed in this invention. Specific syntheses of compounds of this invention and intermediate compounds are illustrated below.

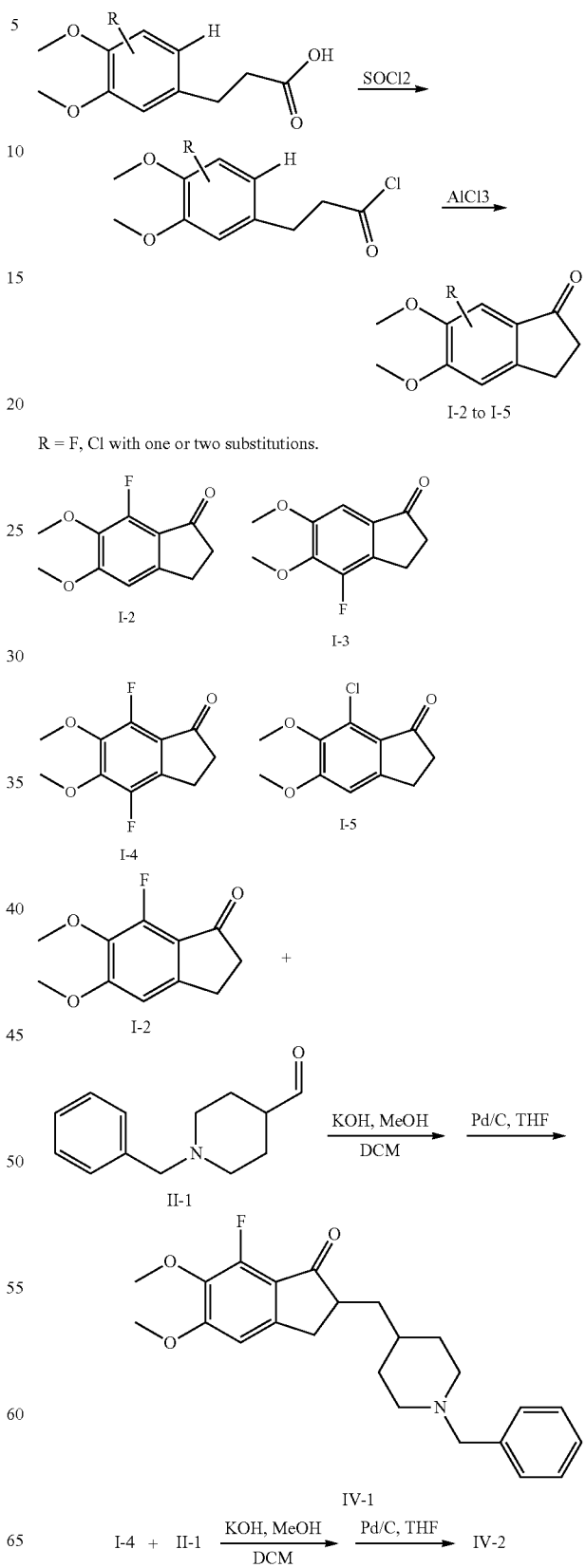

Scheme 5. Synthesis of representative compounds and intermediates of this invention.

R = F, Cl with one or two substitutions.

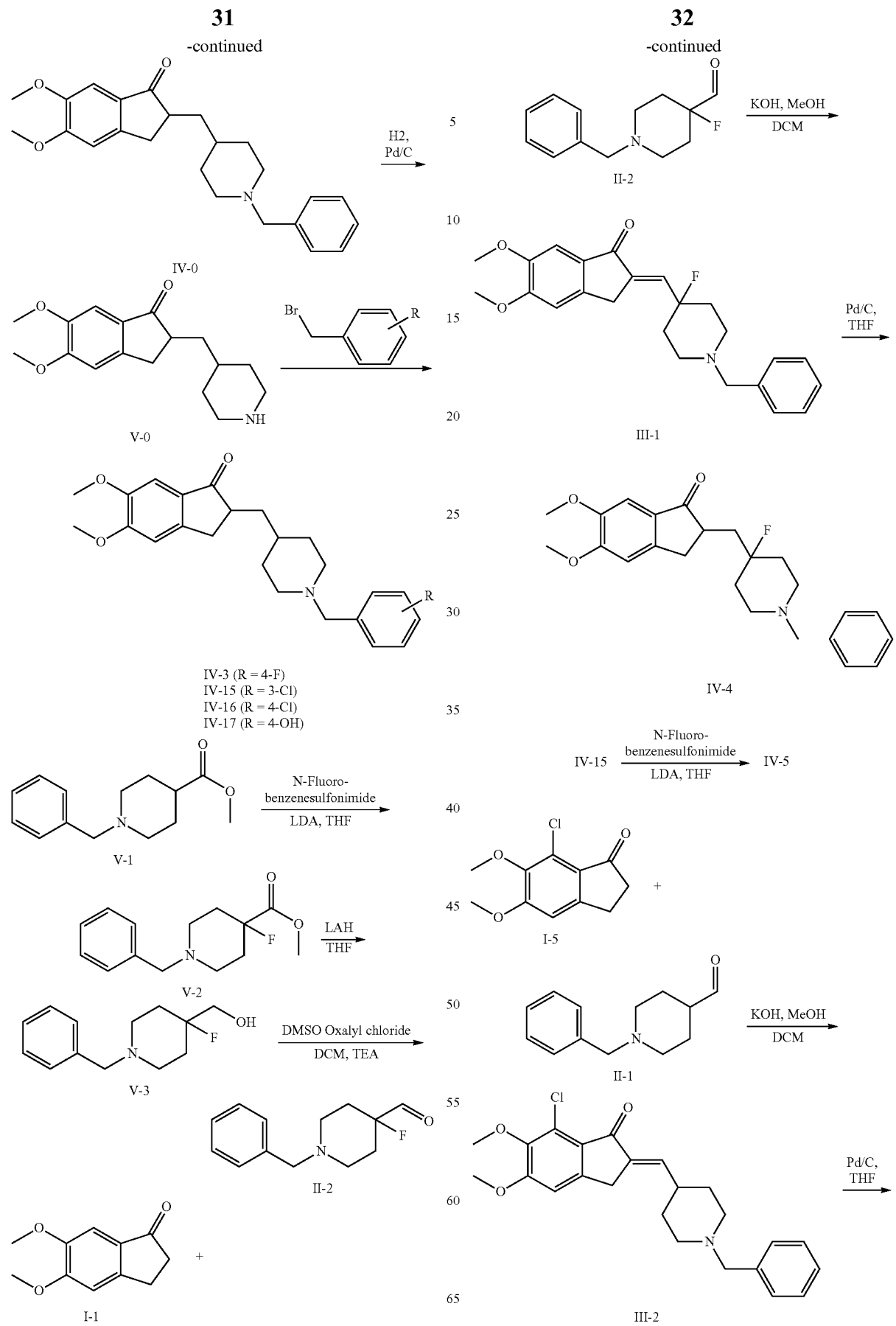

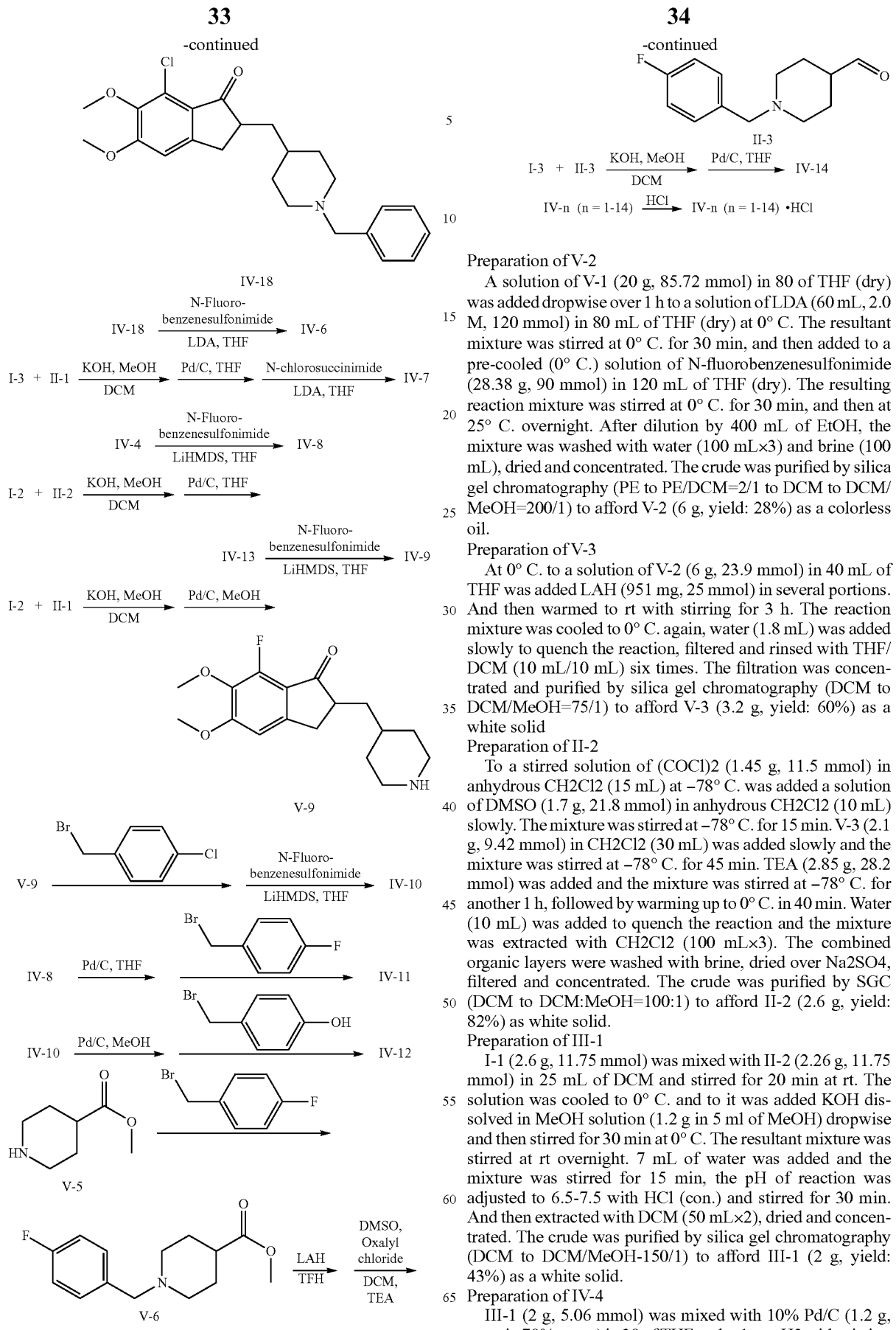

Preparation of V-2

A solution of V-1 (20 g, 85.72 mmol) in 80 of THF (dry) was added dropwise over 1 h to a solution of LDA (60 mL, 2.0 M, 120 mmol) in 80 mL of THF (dry) at 0° C. The resultant mixture was stirred at 0° C. for 30 min, and then added to a pre-cooled (0° C.) solution of N-fluorobenzenesulfonimide (28.38 g, 90 mmol) in 120 mL of THF (dry). The resulting reaction mixture was stirred at 0° C. for 30 min, and then at 25° C. overnight. After dilution by 400 mL of EtOH, the mixture was washed with water (100 mL×3) and brine (100 mL), dried and concentrated. The crude was purified by silica gel chromatography (PE to PE/DCM=2/1 to DCM to DCM/MeOH=200/1) to afford V-2 (6 g, yield: 28%) as a colorless oil.

Preparation of V-3

At 0° C. to a solution of V-2 (6 g, 23.9 mmol) in 40 mL of THF was added LAH (951 mg, 25 mmol) in several portions. And then warmed to rt with stirring for 3 h. The reaction mixture was cooled to 0° C. again, water (1.8 mL) was added slowly to quench the reaction, filtered and rinsed with THF/DCM (10 mL/10 mL) six times. The filtration was concentrated and purified by silica gel chromatography (DCM to DCM/MeOH=75/1) to afford V-3 (3.2 g, yield: 60%) as a white solid Preparation of II-2

To a stirred solution of (COCl)2 (1.45 g, 11.5 mmol) in anhydrous CH2Cl2 (15 mL) at −78° C. was added a solution of DMSO (1.7 g, 21.8 mmol) in anhydrous CH2Cl2 (10 mL) slowly. The mixture was stirred at −78° C. for 15 min. V-3 (2.1 g, 9.42 mmol) in CH2Cl2 (30 mL) was added slowly and the mixture was stirred at −78° C. for 45 min. TEA (2.85 g, 28.2 mmol) was added and the mixture was stirred at −78° C. for another 1 h, followed by warming up to 0° C. in 40 min. Water (10 mL) was added to quench the reaction and the mixture was extracted with CH2Cl2 (100 mL×3). The combined organic layers were washed with brine, dried over Na2SO4, filtered and concentrated. The crude was purified by SGC (DCM to DCM:MeOH=100:1) to afford II-2 (2.6 g, yield: 82%) as white solid.

Preparation of III-1

I-1 (2.6 g, 11.75 mmol) was mixed with II-2 (2.26 g, 11.75 mmol) in 25 mL of DCM and stirred for 20 min at rt. The solution was cooled to 0° C. and to it was added KOH dissolved in MeOH solution (1.2 g in 5 ml of MeOH) dropwise and then stirred for 30 min at 0° C. The resultant mixture was stirred at rt overnight. 7 mL of water was added and the mixture was stirred for 15 min, the pH of reaction was adjusted to 6.5-7.5 with HCl (con.) and stirred for 30 min. And then extracted with DCM (50 mL×2), dried and concentrated. The crude was purified by silica gel chromatography (DCM to DCM/MeOH-150/1) to afford III-1 (2 g, yield: 43%) as a white solid.

Preparation of IV-4

III-1 (2 g, 5.06 mmol) was mixed with 10% Pd/C (1.2 g, contain 70% water) in 30 of THF under 1 atm H2 with stirring at 25° C. overnight. The reaction mixture was filtered and rinsed with MeOH (20 mL×3), the filtration was concentrated. The crude was purified by silica gel chromatography (DCM to DCM/MeOH=150/1) to afford IV-4 (1.45 g, yield: 72%) as a white solid (LC-MS: m/z=398.2123, m/z(calc)= 398.2126).

Preparation of IV-4.HCl

IV-4 (260 mg, 0.65 mmol) was dissolved in 5 mL of MeOH and 0.75 mL of HCl (1M in MeOH) was added. The mixture was concentrated and the precipitation was dried by oil pump to afford IV-4.HCl (293 mg, yield: 93%) as a white-yellow solid (LC-MS: m/z=398.2124, m/z(calc)=398.2126).

Preparation of IV-8

IV-4 (500 mg, 1.26 mmol) was dissolved in 17 mL of THF (dry), was cooled to −78° C., and 2 mL of LiHMDS (1.0 M) was added dropwise. The mixture was raised in temperature from −78° C. to −10° C. over 30 min, was then cooled again to −78° C., and a solution of N-fluorobenzenesulfonimide (635 mg, 2 mmol) in 9 mL of THF was added. The mixture was gradually raised in temperature from −78° C. to 25° C. and stirred at 25° C. overnight. The reaction mixture was treated with saturated NH4Cl (15 mL) and water (15 mL), extracted with EA (50 mL×3), dried and concentrated. The crude was purified by silica gel chromatography (PE/EA=5/1 to 3/1) to afford IV-8 (296 mg, yield: 57%) as a white solid (LC-MS: m/z=416.2030, m/z(calc)=416.2032).

Preparation of IV-8.HCl

IV-8 (295 mg, 0.71 mmol) was dissolved in 5 mL of MeOH and 0.75 mL of HCl (1M in MeOH) was added. The mixture was concentrated and the precipitate was dried by oil pump to afford IV-8.HCl (303 mg, yield: 95%) as a straw-yellow solid (LC-MS: m/z=416.2031, m/z(calc)=416.2032).

Preparation of V-4

IV-8 (295 mg, 0.71 mmol) was dissolved in 15 mL of MeOH and Pd/C (10%) was added. The mixture was stirred violently under Hydrogen atmosphere overnight at room temperature. The catalyst was filtered by celite and washed with MeOH 3 times. The combined solvent was concentrated under reduced pressure to give V-4 (217 mg, yield: 97%).

Preparation of IV-11

V-4 (217 mg, 0.67 mmol) was dissolved in 5 mL of acetone3 and K2CO3 (3 eq) was added. Then 4-fluorobenzyl bromide (1.1 eq) was added. The mixture was stirred under room temperature for 3 h. The starting material was all consumed by TLC. The solvent was removed under reduced pressure and the crude mixture was purified through silica chromatography to give IV-11 (235 mg, yield: 87%) as while solid (LC-MS: m/z=434.1934, m/z(calc)=434.1938).

Preparation of IV-11.HCl

IV-11 (341 mg, 0.79 mmol) was dissolved in 5 mL of MeOH and 0.75 mL of HCl (1M in MeOH) was added. The mixture was concentrated and the precipitate was dried by oil pump to afford IV-11.HCl (322 mg, yield: 92%) as a white solid (LC-MS: m/z=434.1936, m/z(calc)=434.1938).

Preparation of V-9

1-2 (2.9 g, 11.4 mmol) was mixed with II-1 (2.2 g, 12 mmol) in 25 mL of DCM and stirred for 20 min at rt. The solution was cooled to 0° C. and to it was added KOH dissolved in MeOH solution (1.2 g in 5 ml of MeOH) dropwise and then stirred for 30 min at 0° C. The resultant mixture was stirred at rt overnight. 7 mL of water was added and the mixture was stirred for 15 min, the pH of reaction was adjusted to 6.5-7.5 with HCl (con.) and stirred for 30 min. And then extracted with DCM (50 mL×2), dried and concentrated. The crude was purified by silica gel chromatography (DCM to DCM/MeOH=150/1) to afford coupling product (2.2 g, yield: 47%) as a white solid. The coupling product (2.2 g, 5.0 mmol) was dissolved in 15 mL of MeOH and Pd/C (15%) was added. The mixture was stirred violently under hydrogen atmosphere overnight at room temperature. The catalyst was filtered by celite and washed with MeOH 3 times. The combined solvent was concentrated under reduced pressure to give V-9 (1.15 g, yield: 75%) as a white solid.

Preparation of IV-10

V-9 (200 mg, 0.65 mmol) was dissolved in 5 mL of acetone3 and K2CO3 (3 eq) was added. Then 4-chlorobenzyl bromide (1.2 eq) was added. The mixture was stirred under room temperature for 3 h. The starting material was all consumed by TLC. The solvent was removed under reduced pressure and the crude mixture was purified through silica chromatography to give IV-10 (245 mg, yield: 83%) as while solid (LC-MS: m/z=450.1639, m/z(calc)=450.1642).

Preparation of IV-10.HCl

IV-10 (245 mg, 0.55 mmol) was dissolved in 5 mL of MeOH and 0.75 mL of HCl (1M in MeOH) was added. The mixture was concentrated and the precipitate was dried by oil pump to afford IV-10.HCl (265 mg, yield: 96%) as a straw-yellow solid (LC-MS: m/z=450.1641, m/z(calc)=450.1642).

Preparation of IV-12

V-10 (245 mg, 0.55 mmol) was dissolved in 15 mL of MeOH and Pd/C (10%) was added. The mixture was stirred violently under hydrogen atmosphere overnight at room temperature. The catalyst was filtered by celite and washed with MeOH×3. The combined solvent was concentrated under reduced pressure to give de-benzyl product (108 mg, yield: 72%) as a white solid. The de-benzyl product was dissolved in 5 mL of acetone3 and K2CO3 (3 eq) was added. Then 4-hydroxybenzyl bromide (1.2 eq) was added. The mixture was stirred under room temperature for 3 h. The starting material was all consumed by TLC. The solvent was removed under reduced pressure and the crude mixture was purified through silica chromatography to give IV-12 (198 mg, yield: 75%) as while solid (LC-MS: m/z=432.1977, m/z(calc)=432.1981).

Preparation of IV-12.HCl

IV-12 (198 mg, 0.47 mmol) was dissolved in 5 mL of MeOH and 0.65 mL of HCl (1M in MeOH) was added. The mixture was concentrated and the precipitate was dried by oil pump to afford IV-12.HCl (210 mg, yield: 93%) as a straw-yellow solid (LC-MS: m/z=432.1979, m/z(calc)=432.1981).

Example 16

Inhibition of AChE Enzyme Activity

Inhibition of AChE enzyme activity was measured to demonstrate the improved properties of the compounds of this invention. Experimental procedures were described in the embodiments of this invention. IC50 values of selected compounds are listed in Table 3.

TABLE 3

| Inhibition of AChE enzyme activity. | |
|---|---|
| Compound | IC50 (nM) |
| Donepezil | 19.3 |
| IV-4 | 1.04 |
| IV-8 | 9.07 |
| IV-11 | 28.2 |

Example 17

Pharmacokinetics

Pharmacokinetics and bioavailability in rats and mice were done with IV and PO dosing to evaluate the improved properties of the compounds of the invention related to donepezil according to the procedure illustrated in the embodiments. Experimental animal used were male Sprague-Dawley rats from Shanghai Sino-British SIPPR/BK Lab Animal Ltd, approximately 8 weeks of age (180-250 g body weight). Table 4 lists pharmacokinetic parameters of selected compounds of this invention.

TABLE 4

Rat pharmacokinetic parameters of selected compounds.

| Compounds | Dose | T½ hr) | F (%) |
|---|---|---|---|
| Donepezil | IV | 4.08 | 100 |
| | PO | 12.5 | 26.1 |
| | SC | 6.4 | 60.2 |
| IV-8 | IV | 8.5 | 100 |
| | PO | 12.7 | 37.2 |
| | SC | 6.8 | 70.5 |
| IV-11 | IV | 3.1 | 100 |
| | PO | 11.8 | 28.2 |
| | SC | 7.9 | 100 |

T1/2 = terminal half life.
F = oral bioavailability.
IV = intravenous.
PO = oral.
SC = subcutaneous.

FIG. 1 shows plot of plasma concentration vs. time for donepezil and compound IV-8 with intravenous (IV) and oral (PO) dosing on SD rats.

Example 18

Morris Water Maze Experiment on Memory Restoration

Evaluation of the compounds of the invention for memory restoring effect was done by water maze experiment in rats. Compound therapeutic effect on scopolamine-induced impairments of spatial learning and memory was measured according to the procedure illustrated in the embodiments. Experimental animal used were male Male Wistar rats (150-170 g) from Shanghai Sino-British SIPPR/BK Lab Animal Ltd.

FIG. 2 shows experimental data for compound IV-8.

Example 19

Toxicology Measurements

Acute toxicity for selected compounds of this invention was measured in mice according to the procedure illustrated in the embodiments. Male and female CD-1 mice (n=2-5/gender/compound dose, 25-32 grams) were from Shanghai Sino-British SIPPR/BK Lab Animal Ltd. Table 4 lists toxicology study observations for selected compounds.

TABLE 4

LD50 values.

| Compounds | Mouse LD50 (mg/kg) |
|---|---|
| Donepezil | 33 |
| IV-4 | 30 |
| IV-8 | >45 |
| IV-11 | >50 |

REFERENCES CITED

U.S. Patent Documents

Cheng, X. U.S. patent application Ser. No. 12/946,533—Method for improving the properties of a drug lead compound, U.S. patent application on November, 2010, claiming priority benefit of U.S. Provisional Application 61/281, 371, filed on November, 2009.

U.S. Pat. No. 4,895,841 Cyclic amine compounds with activity against acetylcholinesterase Sugimoto, H. et al. Jan. 23, 1990, 209, 339

OTHER REFERENCES

Sujimoto, H, el al. Donepezil Hydrochloride (E2020) and Other Acetylcholinesterase inhibitors, Current Medicinal Chemistry, 2000, 7, 303-339.

Sujinoto, H, et al. Research and Development of Donepezil Hydrochloride, a New Type of Acetylcholinesterase Inhibitor, Jpn. J. Pharmacol. 89, 7-20 (2002).

Ellman, G. L.; et al. A new and rapid colorimetric determination of acetylcholinesterase activity. Biochem. Pharmacol. 1961, 7, 88-95.

Holzgrabe, U. et al., NMR spectroscopy in drug development and analysis, Wiley-VCH, 1999, Weinheim.

Lee, M. S. Integrated Strategies for Drug Discovery Using Mass Spectrometry, Wiley-Interscience, 2005.

Wanner, K. et al., Mass Spectrometry in Medicinal Chemistry: Applications in Drug Discovery, Volume 36, Wiley Interscience, 2007.

Desiderio, D. M. and Nibbering, N. M. "Mass Spectrometry: Instrumentation, interpretation, and Applications" Wiley Interscience, 2008, ISBN: 0471713951

McLafferty, F. W. and Tureek, F. "interpretation of Mass Spectra" 4th edition, University Science Books, 1993.

R. G. M. Morris, Development of a water-maze procedure for studying spatial learning in the rat, J Neurosci Meth, 1984. 11:47-60.

R. K. McNamara and R. W. Skelton, The neuropharmacological and neurochemical basis of place learning in the Morris water maze, Brain Res Rev, 1993. 18:33-49.

Shintani, E. Y., et al. 1997. Am J Health Syst Pharm. 54: 2805-2810. PMID: 9428950

Bryson, H. M. and Benfield, P. 1997. Drugs Aging. 10: 234-240. PMID: 9108896.

Larock R, Comprehensive Organic Transformations, VCH Publishers (1989).

Greene T W et al., Protective Groups in Organic Synthesis, 3rd Ed., John Wiley and Sons (1999).

Fieser L., et al., Fieser and Fieser's Reagents for Organic Synthesis, John Wiley and Sons (1994).

Paquette L, ed., Encyclopedia of Reagents for Organic Synthesis, John Wiley and Sons (1995).

Corey, E. J. and Cheng, X.-M., The Logic of Chemical Synthesis, Wiley, New York, 1989.

A. L. Simplicio, et al., Prodrugs for Amines, Molecules 2008, 13, 519-547.

The invention claimed is:
1. A compound of Formula I, II or III:

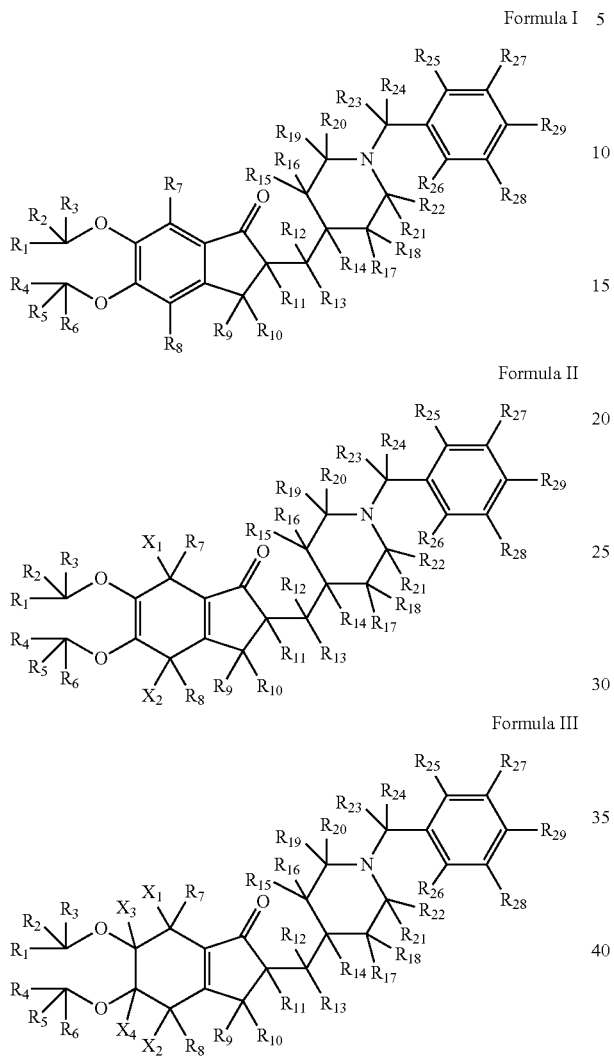

wherein: R1-R29 and X1-X4 are independently selected from hydrogen, deuterium, $C_{1-12}$ alkyl, $C_{1-12}$ alkoxy, aryloxy, trifluoromethyl, trifluoromethoxy, cyano, nitro, $C_{1-12}$ alkylamino, $C_{1-12}$ dialkylamino, $C_{1-12}$ alkylthio, arylthio, $C_{1-12}$ alkylcarbonyl, arylcarbonyl, $C_{1-12}$ alkylcarboxy, arylcarboxy, $C_{1-12}$ alkoxylcarboxy, aryloxylcarboxy, $C_{1-12}$ alkanoylamino, arylcarbonylamino, $C_{1-12}$ alkylcarbamido, arylcarbamido, $C_{1-12}$ alkylaminocarboxy, arylaminocarboxy, trifluoroacetyl, halogen, $C_{1-12}$ alkoxylcarbonyl, aryloxycarbonyl, $C_{1-12}$ alkysulfinyl, arylsulfinyl, $C_{1-12}$ alkylsulfonyl, arylsulfonyl, $C_{1-12}$ alkylsulfonamido, arylsulfonamido, and aryl functional groups;
and wherein R14 in formula I is not hydrogen;
or a N-oxide thereof; or a pharmaceutically acceptable salt thereof.

2. The compound of claim 1 wherein: R1-R29 and X1-X4 are independently selected from hydrogen, deuterium, methyl, methoxy, aryloxy, trifluoromethyl, trifluoromethoxy, cyano, nitro, amino, mercapto, arylthio, formyl, acetyl, arylcarbonyl, formate, arylcarboxy, lower alkoxylcarboxy, aryloxylcarboxy, formamido, arylcarbonylamino, carbamido, arylcarbamido, animocaboxy, arylaminocarboxy, trifluoroacetyl, halogen, hydroxylcarbonyl, aryloxycarbonyl, sulfinyl, arylsulfinyl, sulfonyl, arylsulfonyl, sulfonamido, arylsulfonamido and aryl functional groups.

3. The compound of claim 1 selected from:
(1)  2-((1-benzyl-4-fluoropiperidin-4-yl)methyl)-5,6-dimethoxy-2,3-dihydro-1H-inden-1-one

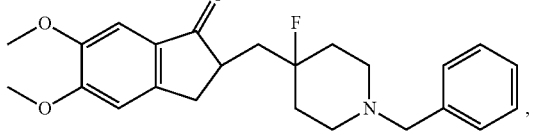

(2) 2-((1-benzyl-4-fluoropiperidin-4-yl)methyl)-2-fluoro-5,6-dimethoxy-2,3-dihydro-1H-inden-1-one

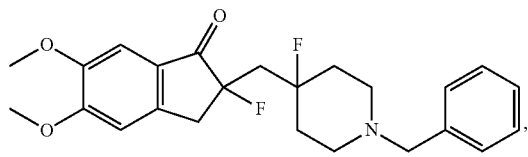 [SMILES: COc1cc2c(cc1OC)C(=O)C(F)(CC1(F)CCN(Cc3ccccc3)CC1)C2]

(3)  2-((1-benzyl-4-fluoropiperidin-4-yl)methyl)-2,7-difluoro-5,6-dimethoxy-2,3-dihydro-1H-inden-1-one

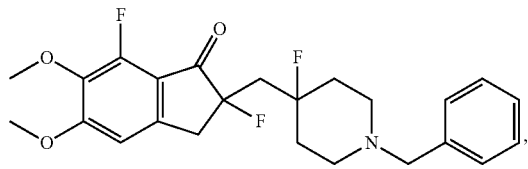 [SMILES: COc1cc2c(c(F)c1OC)C(=O)C(F)(CC1(F)CCN(Cc3ccccc3)CC1)C2]

(4)  2-fluoro-2-((4-fluoro-1-(4-fluorobenzyl)piperidin-4-yl)methyl)-5,6-dimethoxy-2,3-dihydro-1H-inden-1-one

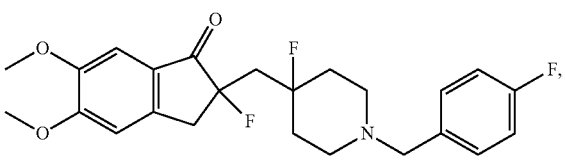 [SMILES: COc1cc2c(cc1OC)C(=O)C(F)(CC1(F)CCN(Cc3ccc(F)cc3)CC1)C2]

(5) 2-((1-benzyl-4-fluoropiperidin-4-yl)methyl)-7-fluoro-5,6-dimethoxy-2,3-dihydro-1H-inden-1-one

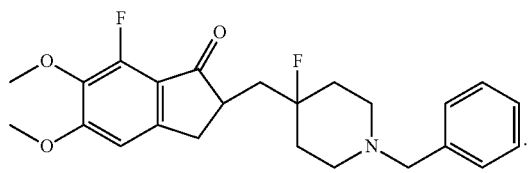 [SMILES: COc1cc2c(c(F)c1OC)C(=O)C(CC1(F)CCN(Cc3ccccc3)CC1)C2]

4. A pharmaceutical composition comprising:
a compound of claim 1; and
a pharmaceutically acceptable carrier.

5. The pharmaceutical composition of claim 4 further comprising one or more additional therapeutic agents.

6. A method of treating Alzheimer's disease by administering an acetylcholinesterase (AChE) inhibitor in a patient in need thereof comprising: administering to the patient an effective amount of the pharmaceutical composition of claim 4.

* * * * *